(12) United States Patent
Tsai et al.

(10) Patent No.: US 10,069,090 B2
(45) Date of Patent: Sep. 4, 2018

(54) ORGANIC ELECTROLUMINESCENT MATERIALS AND DEVICES

(71) Applicant: Universal Display Corporation, Ewing, NJ (US)

(72) Inventors: Jui-Yi Tsai, Newtown, PA (US); Chuanjun Xia, Lawrenceville, NJ (US); Miguel A. Esteruelas, Saragossa (ES)

(73) Assignee: Universal Display Corporation, Ewing, NJ (US)

( * ) Notice: Subject to any disclaimer, the term of this patent is extended or adjusted under 35 U.S.C. 154(b) by 859 days.

(21) Appl. No.: 14/075,653

(22) Filed: Nov. 8, 2013

(65) Prior Publication Data
US 2014/0138653 A1 May 22, 2014

Related U.S. Application Data

(60) Provisional application No. 61/728,411, filed on Nov. 20, 2012.

(51) Int. Cl.
| | | |
|---|---|---|
| *B32B 9/00* | (2006.01) | |
| *B32B 19/00* | (2006.01) | |
| *H01L 51/00* | (2006.01) | |
| *C09K 11/06* | (2006.01) | |
| *C07F 15/00* | (2006.01) | |
| *H01L 51/50* | (2006.01) | |

(52) U.S. Cl.
CPC ........ *H01L 51/0088* (2013.01); *C07F 15/002* (2013.01); *C09K 11/06* (2013.01); *C09K 2211/1007* (2013.01); *C09K 2211/1029* (2013.01); *C09K 2211/1044* (2013.01); *C09K 2211/185* (2013.01); *H01L 51/5016* (2013.01)

(58) Field of Classification Search
CPC combination set(s) only.
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0151042 A1 | 8/2003 | Marks et al. | |
| 2003/0152802 A1 | 8/2003 | Tsuboyama et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Table of Valences of Elements ("sciencenotes.org/valences-of-the-elements").*
Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).

(Continued)

*Primary Examiner* — Austin Murata
(74) *Attorney, Agent, or Firm* — Duane Morris LLP

(57) ABSTRACT

A novel compound having the formula $Os(L)_n$ is disclosed, wherein Os is osmium(IV) metal, L is a ligand coordinating to the Os atom, and n is an integer from 1 to 6, wherein each L can be same or different, wherein at least one L is a multidentate ligand, and wherein the compound is neutral.

19 Claims, 3 Drawing Sheets

(56) References Cited

U.S. PATENT DOCUMENTS

| | | | |
|---|---|---|---|
| 2005/0244673 A1 | 11/2005 | Satoh et al. | |
| 2005/0260441 A1 | 11/2005 | Thompson et al. | |
| 2005/0260449 A1* | 11/2005 | Walters | C09K 11/06 428/690 |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Pakash et al. | |
| 2009/0108737 A1 | 4/2009 | Kwong et al. | |
| 2009/0115316 A1 | 5/2009 | Zheng et al. | |
| 2009/0115322 A1 | 5/2009 | Walters et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2011/0266526 A1* | 11/2011 | Ma | C09K 11/06 257/40 |
| 2012/0004407 A1* | 1/2012 | Stoessel | C07F 5/022 544/225 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 2001039234 | 5/2001 |
| WO | 2002002714 | 1/2002 |
| WO | 200215645 | 2/2002 |
| WO | 2003040257 | 5/2003 |
| WO | 2003060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009046266 A1 | 4/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

(56) References Cited

OTHER PUBLICATIONS

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15)2280-2282 (2000).

Lo, Shih-Chun et al., "Blue Phosphorescence from Iridium(III) Complexes at Room Temperature," Chem. Mater., 18 (21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5''-Bis (dimesitylboryl)-2,2'5',2''-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69(15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

ORGANIC ELECTROLUMINESCENT MATERIALS AND DEVICES

CROSS-REFERENCE TO RELATED APPLICATIONS

According to the provisions of 35 U.S.C. 119(e), this application claims the benefit of U.S. Provisional Application Ser. No. 61/728,411 filed Nov. 20, 2012 the disclosure of which is incorporated herein by reference in its entirety.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds for use as emitters and devices, such as organic light emitting diodes, including the same. More particularly, the compounds disclosed herein are novel phosphorus containing bis(tridentate) osmium complexes.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

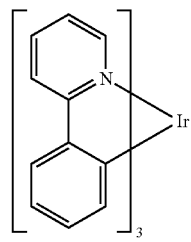

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

According to an embodiment, a compound having the formula $Os(L)_n$ is disclosed; wherein Os is Osmium (IV) metal, L is a ligand coordinating to the Os atom, and n is an integer from 1 to 6; wherein each L can be same or different; wherein at least one L is a multidentate ligand; and wherein the compound is neutral.

According to another aspect, a first device comprising a first organic light emitting device is provided. The first organic light emitting device can comprise an anode, a cathode, and an organic layer, disposed between the anode and the cathode. The organic layer can comprise a compound having the formula $Os(L)_n$, wherein Os is Osmium (IV) metal, L is a ligand coordinating to the Os atom, and n is an integer from 1 to 6, wherein each L can be same or different, wherein at least one L is a multidentate ligand, and wherein the compound is neutral. The first device can be a consumer product, an organic light-emitting device, and/or a lighting panel.

Many osmium(II) based phosphorescent emitters for OLED applications are known. However, because of the shallow HOMO level of Os(II) resulting in a small band gap, tuning the color of the emission of osmium(II) based emitters to blue region can be difficult. The inventors have found that osmium(IV) complexes have deeper HOMO than Os(II) and therefore, it is easier to achieve blue emission. Compared to Os(II) based emitters, Os(IV) complexes have deeper HOMO which enables the incorporation of main stream organic hosts; i.e. a host with HOMO level around −5.39 eV and LUMO level around −1.21 eV. Also, because of the deeper HOMO, OLEDs utilizing Os(IV) based emitters are more immune from formation of exciplex in the device. Os(IV) complexes in general is more difficult to oxidize than Os(II) complexes because of the higher oxidation state; therefore; the band gap is potentially wider than Os(II) and easier to achieve blue emission than Os(II).

Since Os(II) complexes in general has a very shallow HOMO level. It's very difficult to tune emission energy to blue region due to the small band gap. On the other hand, HOMO level of Os(IV) complexes are deeper and potentially easier to reach blue region.

Osmium(II) complexes have been investigated for OLED applications. The octahedral ligand arrangement of the Os(II) complexes resembles that of Ir(III) complexes. Os(II) complexes generally exhibit low oxidation potential, i.e. shallow HOMO energy level than Ir(III) complexes. Os(IV) complexes offers a great deal of flexibility for color tuning and bring the HOMO level to proper alignment in the device.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
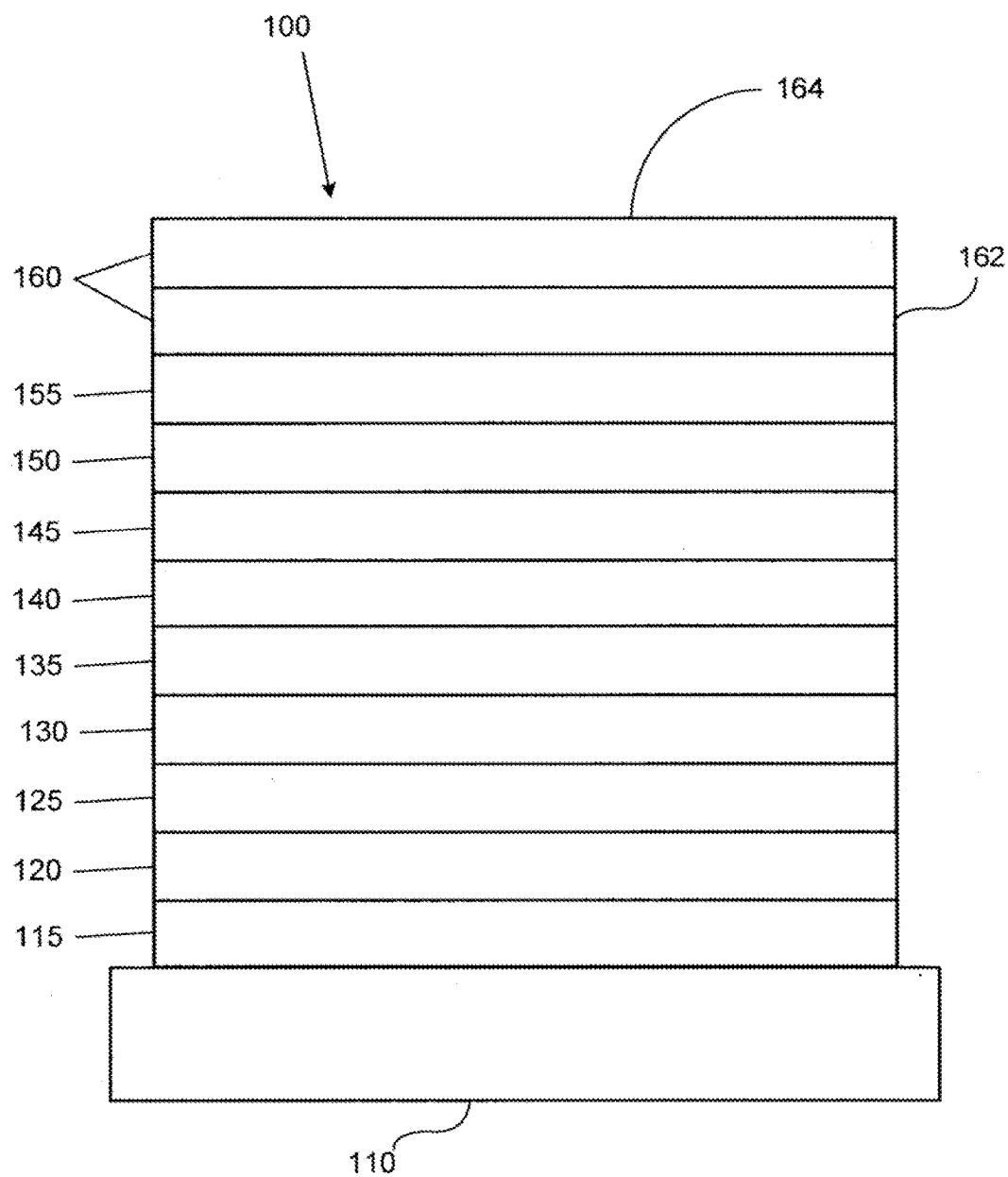
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
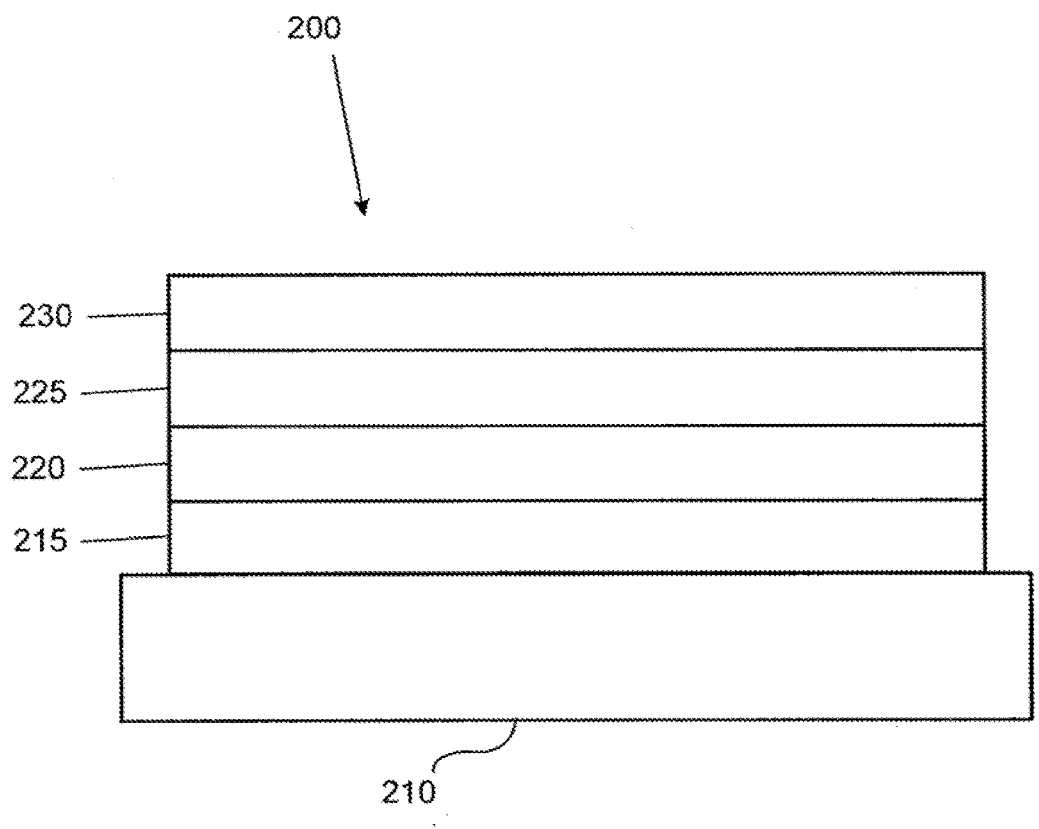
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, aralkyl, heterocyclic group, aryl, aromatic group, and heteroaryl are known to the art, and are defined in U.S. Pat. No. 7,279,704 at cols. 31-32, which are incorporated herein by reference.

As used herein, "substituted" indicates that a substituent other than H is bonded to the relevant carbon. Thus, where $R^2$ is monosubstituted, then one $R^2$ must be other than H. Similarly, where $R^3$ is disubstituted, then two of $R^3$ must be other than H. Similarly, where $R^2$ is unsubstituted $R^2$ is hydrogen for all available positions.

According to an aspect of the present disclosure, a novel compound which is an osmium(IV) complex having the formula $Os(L)_n$ is disclosed; wherein Os is osmium(IV) metal, L is a ligand coordinating to the Os atom, and n is an integer from 1 to 6; wherein each L can be same or different; wherein at least one L is a multidentate ligand; and wherein the compound is neutral.

In one embodiment, the multidentate ligand L of the Os(IV) complex is selected from the group AA consisting of:

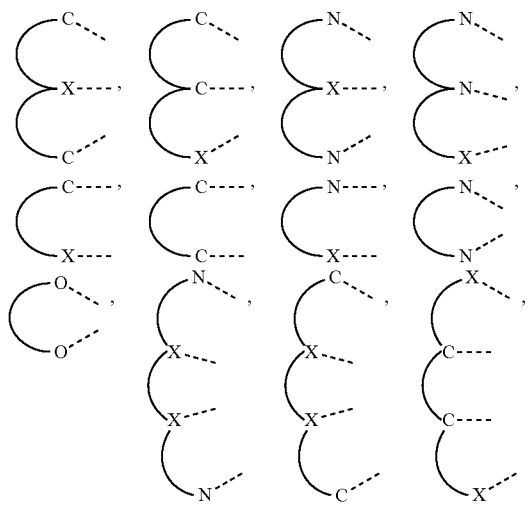

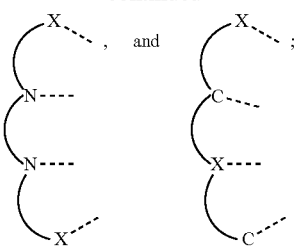

wherein X is a neutral coordinating atom selected from the group consisting of carbene, phosphorus, and nitrogen;

wherein C is an anionic coordinating carbon atom;

wherein N is an anionic coordinating nitrogen atom;

wherein O is an anionic coordinating oxygen atom; and

In one embodiment of the group AA, the neutral carbene is N-heterocyclic carbene; the neutral phosphorus is phosphorus atom of a trisubstituted phosphine; and the neutral nitrogen is $sp^2$ nitrogen atom of N-heterocyclic ring selected from the group consisting of pyridine, imidazole, benzoimidazole, pyrazole, and triazole. The anionic coordinating carbon can be $sp^2$ carbon atom selected from the group consisting of benzene, pyridine, furan, thiophene, and pyrrole. The anionic coordinating nitrogen can be $sp^2$ nitrogen atom of N-heterocyclic ring selected from the group consisting of imidazole, benzoimidazole, pyrazole, and triazole. The anionic oxygen atom can be oxygen atom from carboxylic acid or ether.

In another embodiment of the osmium(IV) complex having the formula $Os(L)_n$, wherein the multidentate ligand L is selected from the group AA, n is 2 and each L is a tridentate ligand. In such embodiment, the osmium(IV) complex compound can have a formula selected from the group consisting of:

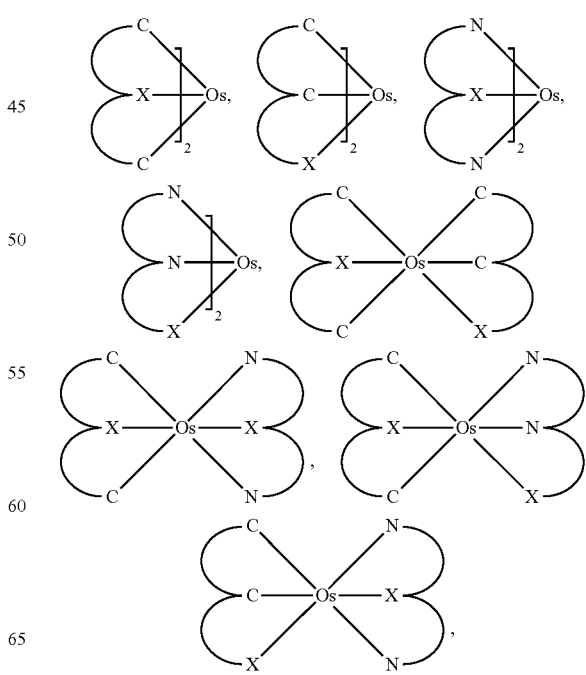

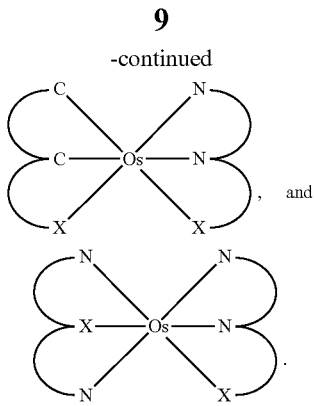
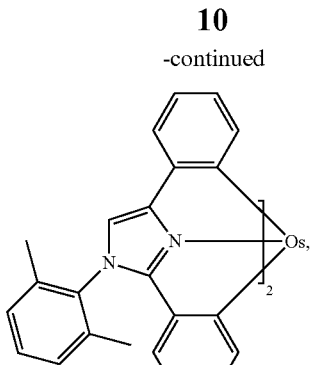
Compound I-4
Where the osmium(IV) complex having the formula Os(L)$_n$, wherein the multidentate ligand L is selected from the group AA, and n is 2 and each L is a tridentate ligand, the osmium(IV) complex compound can be selected from the group consisting of:
Compound I-1
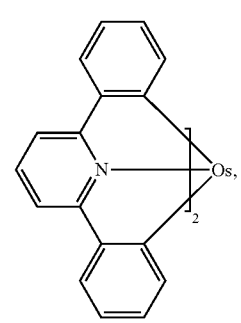
Compound I-5
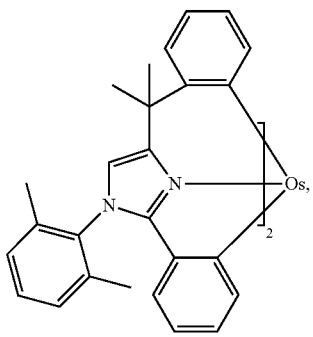
Compound I-2
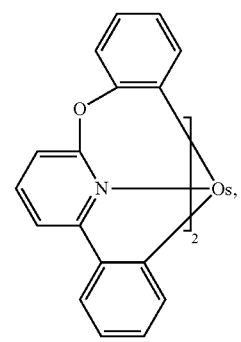
Compound I-6
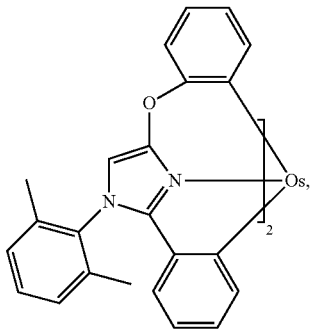
Compound I-3
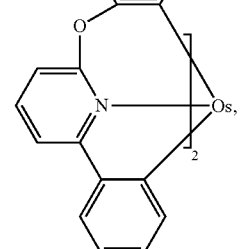
Compound I-7
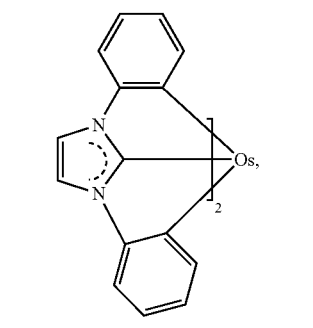
Compound I-8
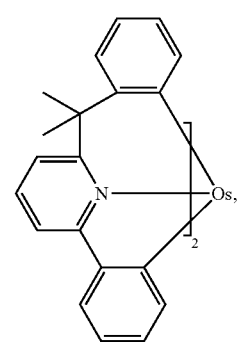
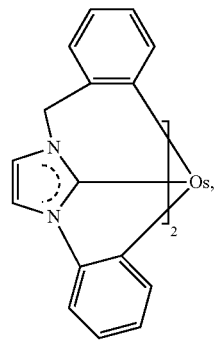

-continued
Compound I-9
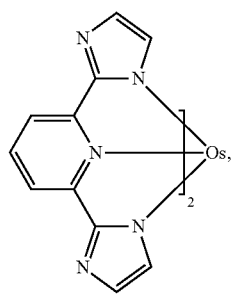
Compound I-10
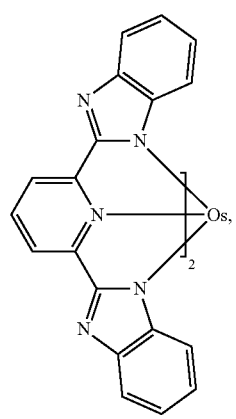
Compound I-11
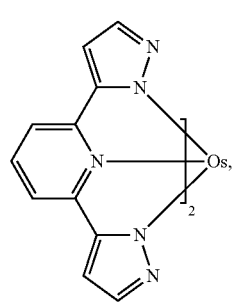
Compound I-12
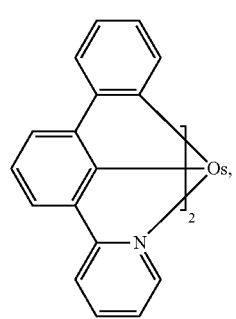
Compound I-13
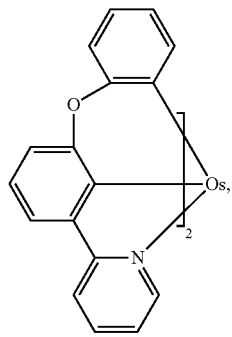
Compound I-14
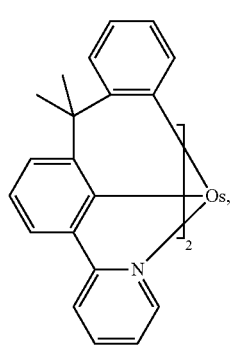
Compound I-15
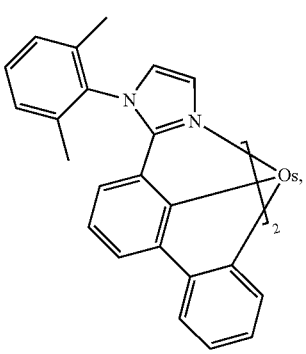
Compound I-16
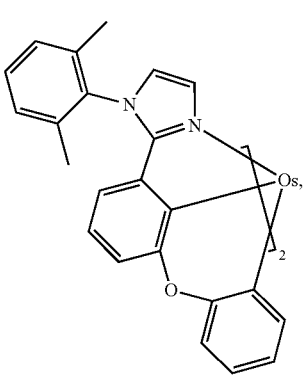

Compound I-17
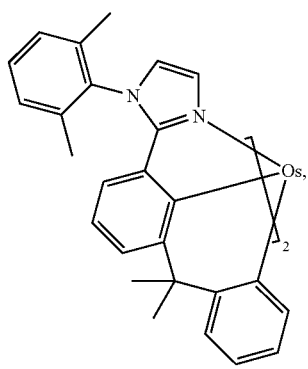
Compound I-18
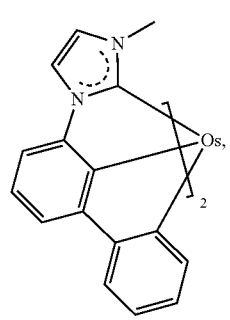
Compound I-19
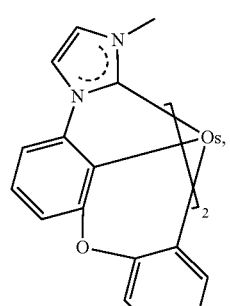
Compound I-20
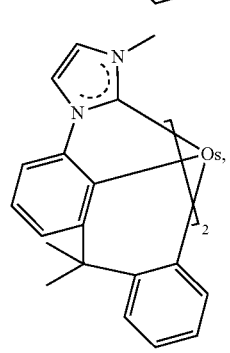
Compound I-21
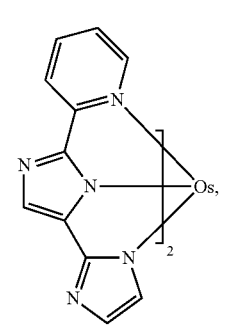
Compound I-22
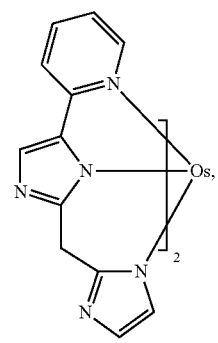
Compound I-23
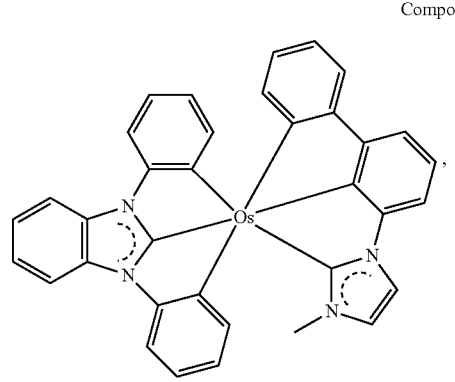
Compound I-24
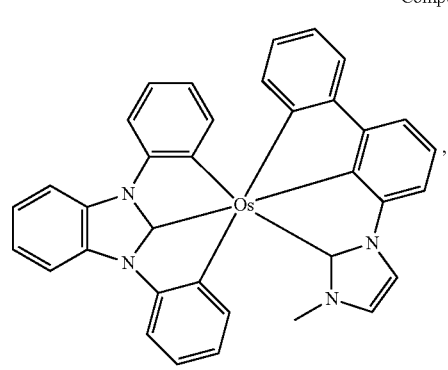
Compound I-25
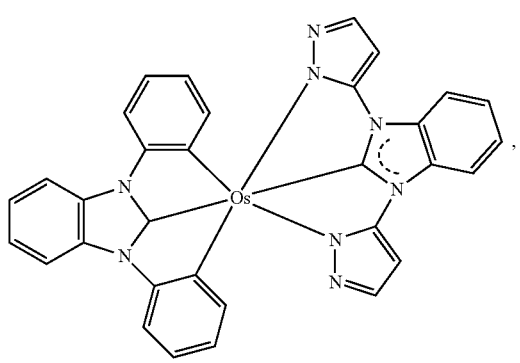

-continued

Compound I-26

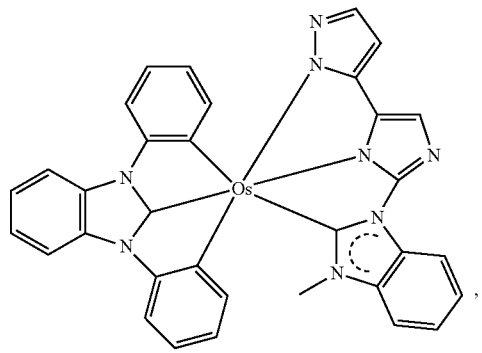

Compound I-27

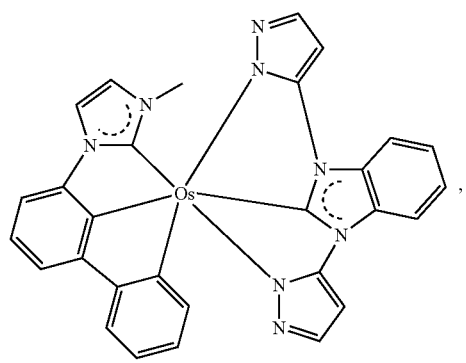

Compound I-28

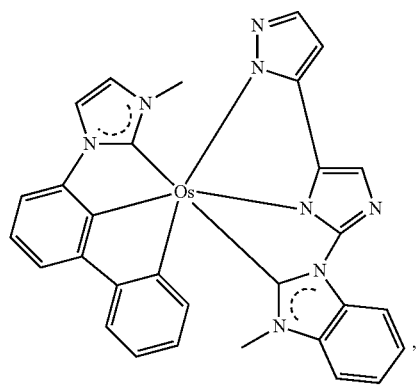

and

Compound I-29

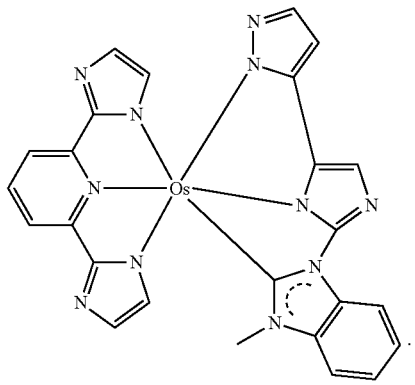

In another embodiment, the osmium(IV) complex compound has the formula Os(L)$_n$, wherein the multidentate ligand L is selected from the group AA, and n is 3 and each L is a bidentate ligand. In such embodiment, the osmium(IV) complex compound can have a formula selected from the group consisting of:

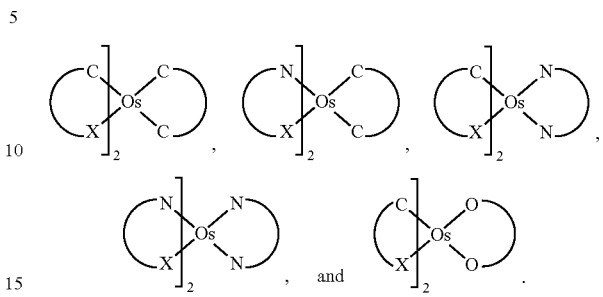

Where the osmium(IV) complex is a compound having the formula Os(L)$_n$ where the multidentate ligand L is selected from the group AA, and n is 3 and each L is a bidentate ligand, the osmium(IV) complex compound can be selected from the group consisting of:

Compound II-1

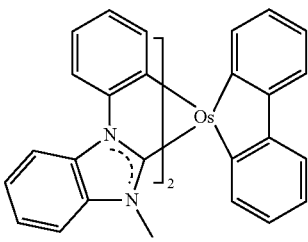

Compound II-2

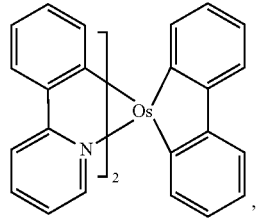

Compound II-3

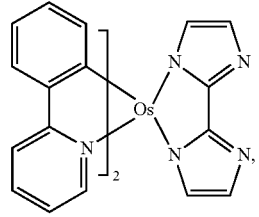

Compound II-4

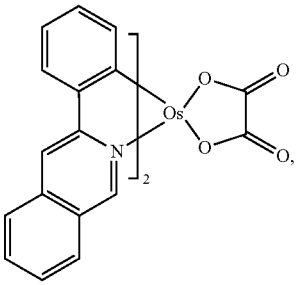

-continued

Compound II-5

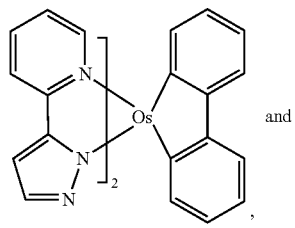

and

Compound II-6

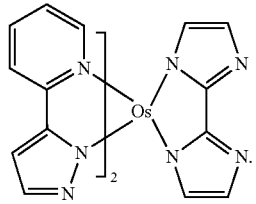

In one embodiment, the osmium(IV) complex is a compound having the formula Os(L)$_n$, wherein the multidentate ligand L is selected from the group AA, and wherein n is 3 and one L is a tridentate ligand and two Ls are bidentate ligand. In such embodiment, the osmium(IV) complex compound can have a formula selected from the group consisting of:

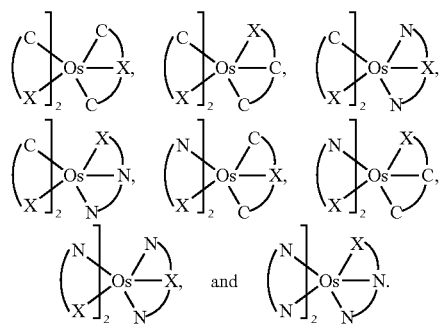

Where the osmium(IV) complex is a compound having the formula Os(L)$_n$, wherein the multidentate ligand L is selected from the group AA, and n is 3 and one L is a tridentate ligand and two Ls are bidentate ligand, the compound can be selected from the group consisting of:

Compound III-1

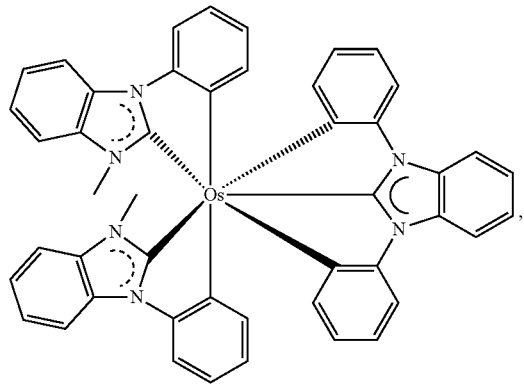

-continued

Compound III-2

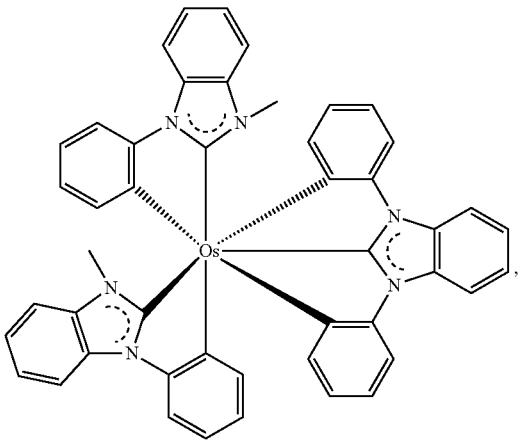

Compound III-3

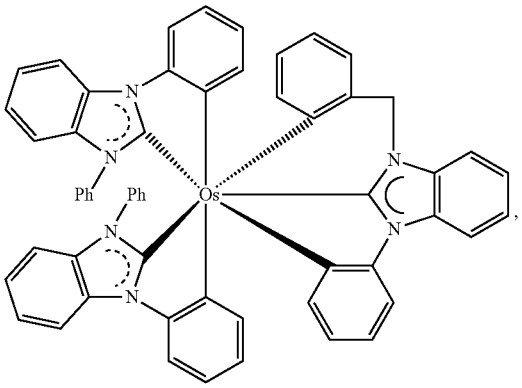

Compound III-4

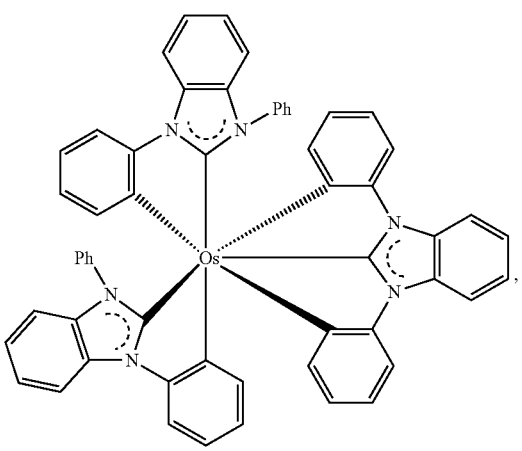

Compound III-5
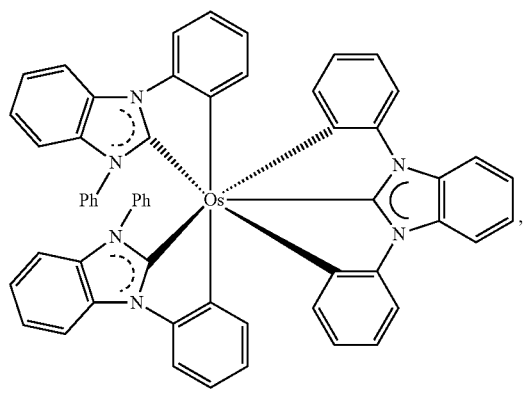
Compound III-6
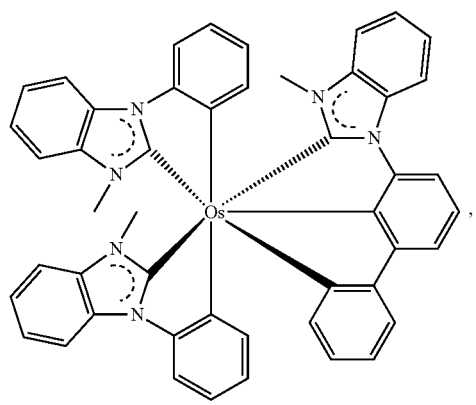
Compound III-7
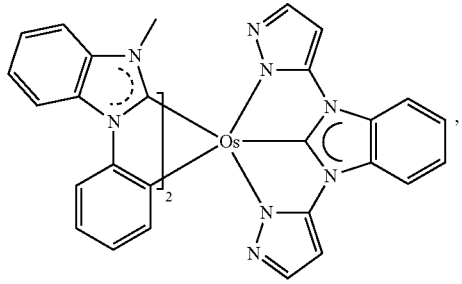
Compound III-8
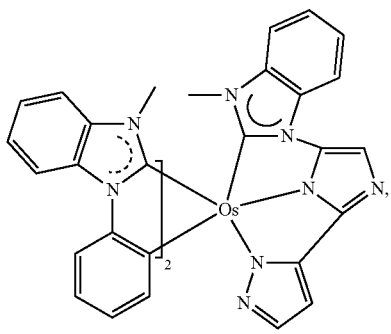
Compound III-9
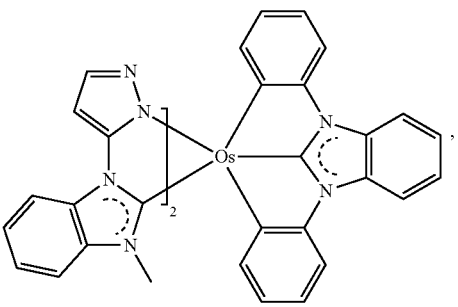
Compound III-10
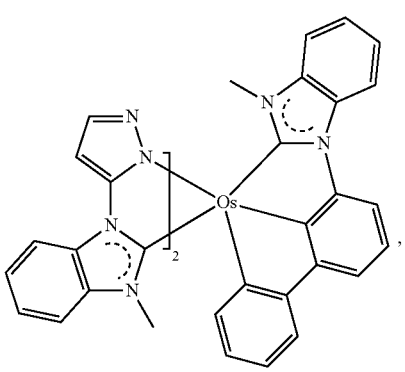
Compound III-11
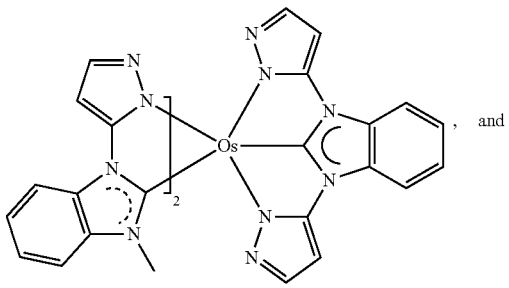
and
Compound III-12
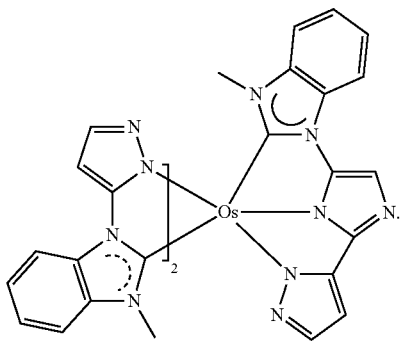

Compound III-13

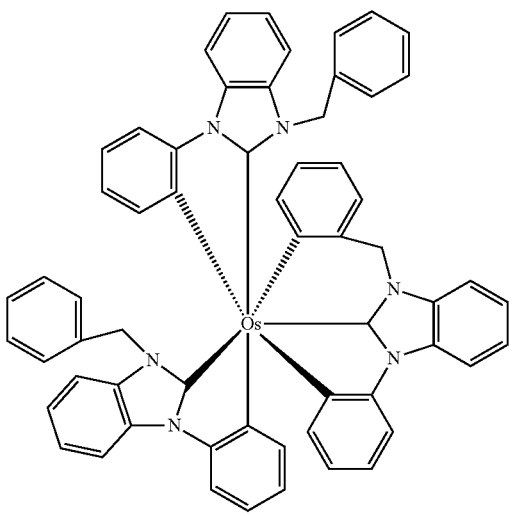

Compound IV-1

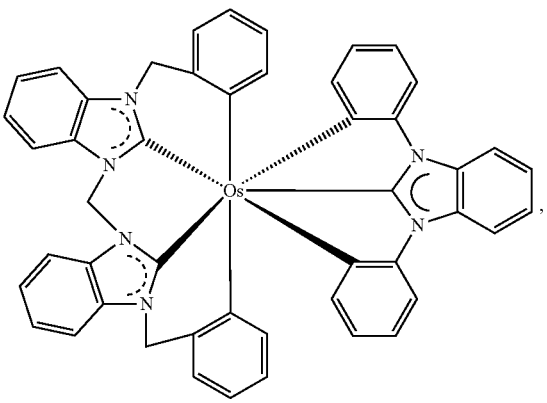

Compound IV-2

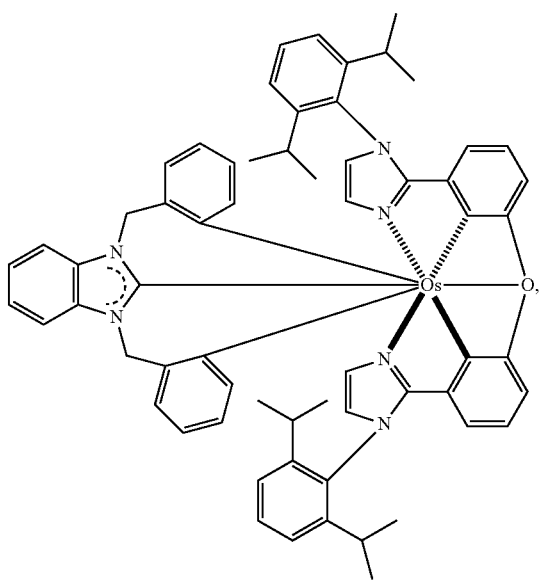

Compound IV-3

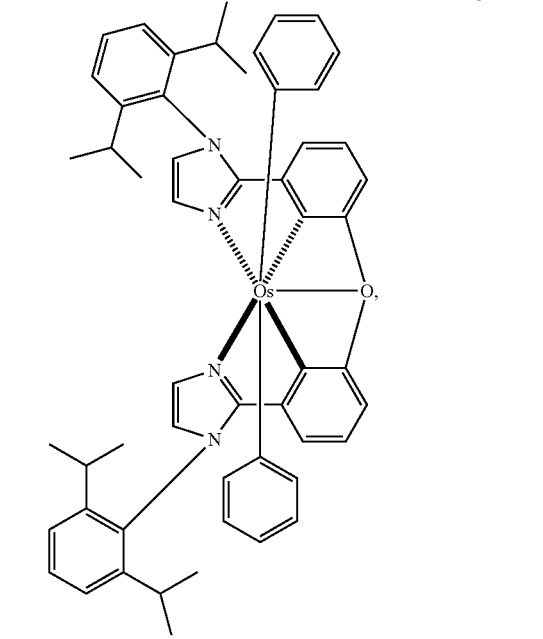

In one embodiment, the osmium(IV) complex is a compound having the formula Os(L)$_n$, wherein the multidentate ligand L is selected from the group AA, and wherein one L is a tetradentate ligand. In such embodiment, the compound can have a formula selected from the group consisting of:

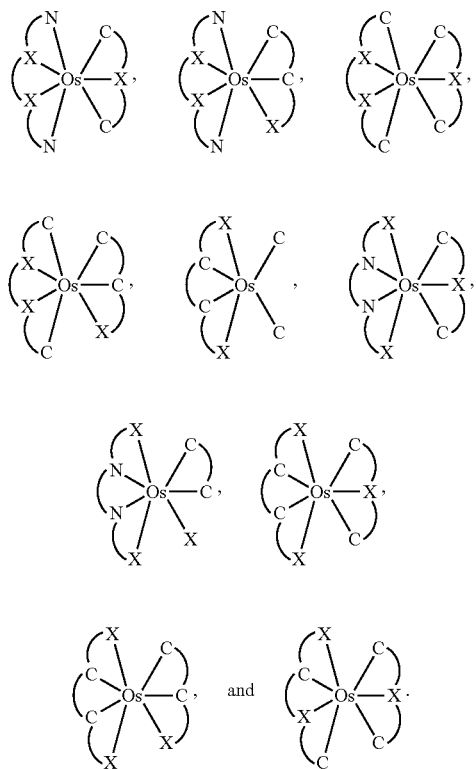

In the embodiment where the osmium(IV) complex is a compound having the formula Os(L)$_n$, wherein the multidentate ligand L is selected from the group AA, and one L is a tridentate ligand, the compound can be selected from the group consisting of:

Compound IV-4
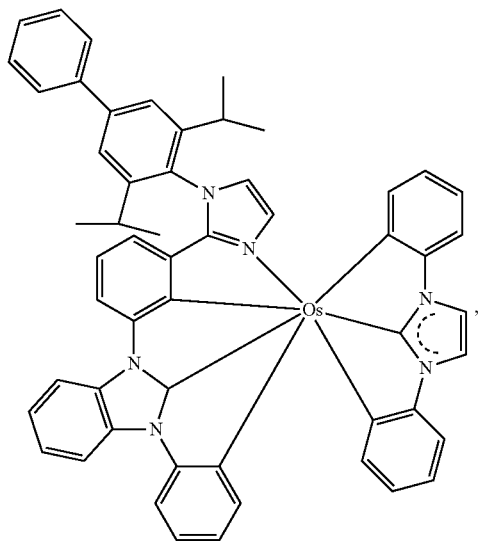
Compound IV-5
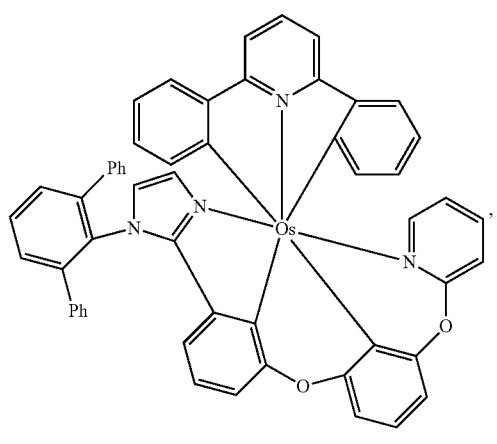
Compound IV-6
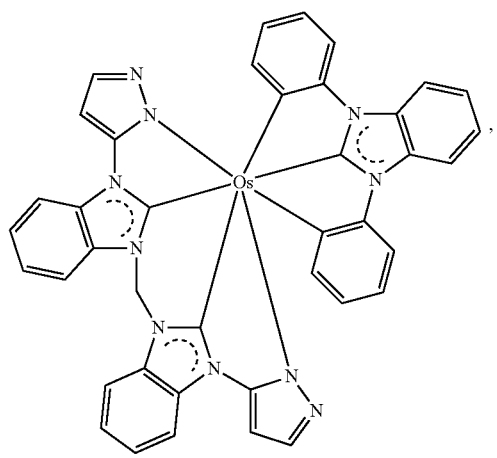
Compound IV-7
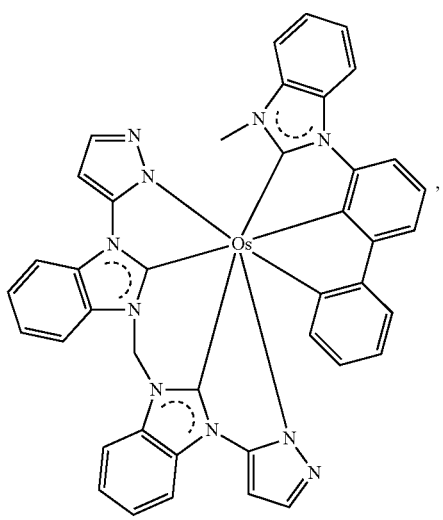
Compound IV-8
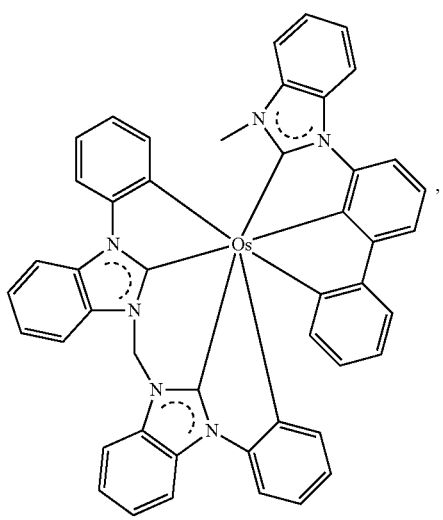
Compound IV-9
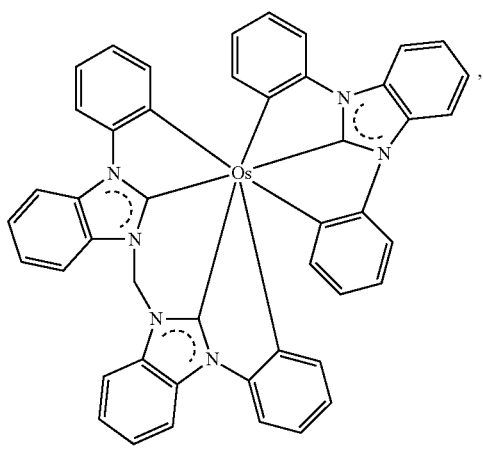

-continued

Compound IV-10

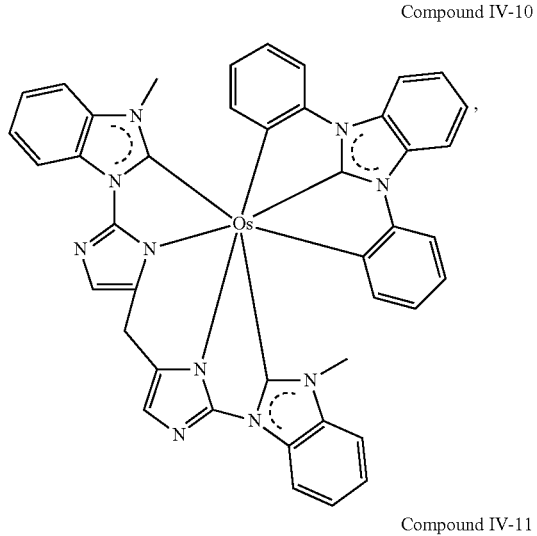

Compound IV-11

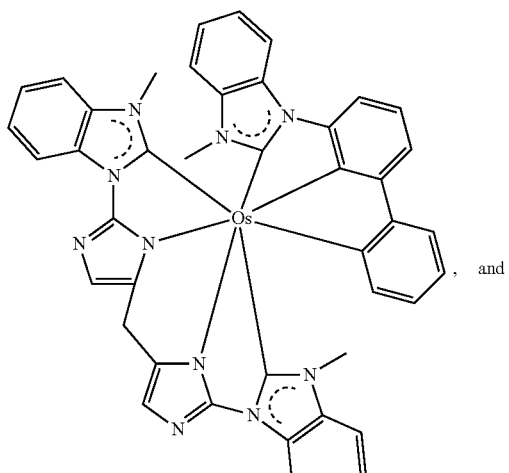, and

Compound IV-12

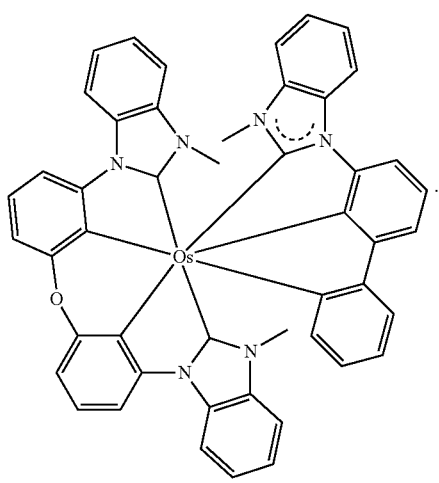

In one embodiment, the osmium(IV) complex compound having the formula Os(L)$_n$, wherein the multidentate ligand L is selected from the group AA, has a formula

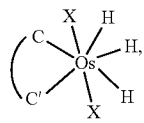

wherein H is hydride. In such embodiment, the compound can be selected from the group consisting of:

Compound V-1

Compound V-2

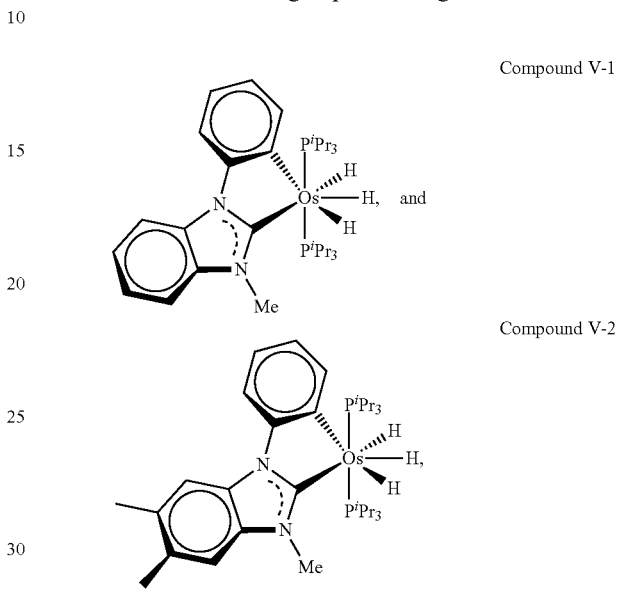

According to another aspect, a first device comprising a first organic light emitting device is provided. The first organic light emitting device can comprise an anode, a cathode, and an organic layer, disposed between the anode and the cathode. The organic layer can comprise a compound having the formula Os(L)$_n$, wherein Os is Osmium (IV) metal, L is a ligand coordinating to the Os atom, and n is an integer from 1 to 6, wherein each L can be same or different, wherein at least one L is a multidentate ligand, and wherein the compound is neutral. The first device can be a consumer product, an organic light-emitting device, and/or a lighting panel.

In one embodiment of the first device, the organic layer is an emissive layer and the compound having the formula Os(L)$_n$ is an emissive dopant. In another embodiment, the organic layer is an emissive layer and the compound having the formula OS(L)$_n$ is a non-emissive dopant.

In another embodiment of the first device, the organic layer further comprises a host material. The host material can comprise a triphenylene containing benzo-fused thiophene or benzo-fused furan; wherein any substituent in the host material is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, and $C_nH_{2n}-Ar_1$, or the host has no substitutions;

wherein n is from 1 to 10; and wherein $Ar_1$ and $Ar_2$ are independently selected from the group consisting of benzene, biphenyl, naphthalene, triphenylene, carbazole, and heteroaromatic analogs thereof.

In another embodiment, the host material comprises at least one chemical group selected from the group consisting of carbazole, dibenzothiophene, dibenzofuran, dibenzoselenophene, azacarbazole, aza-dibenzothiophene, aza-dibenzo-furan, and aza-dibenzoselenophene.
In another embodiment, the host material is selected from the group consisting of
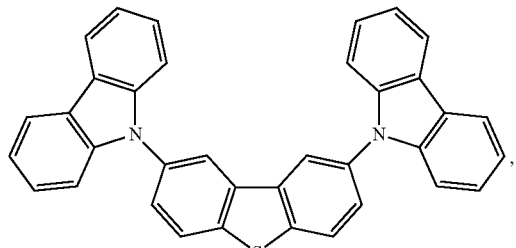
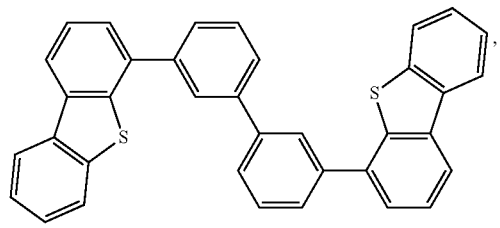
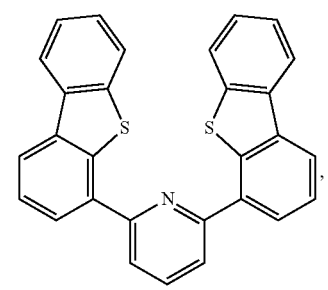
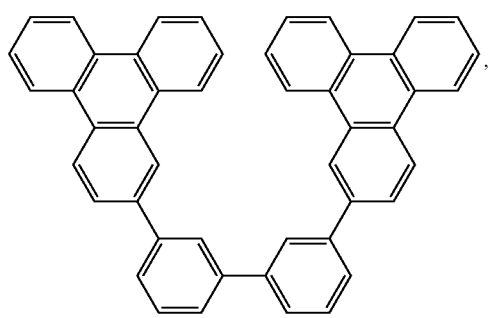
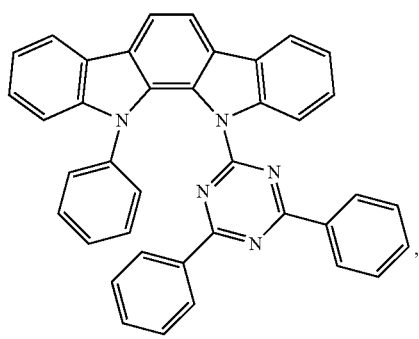
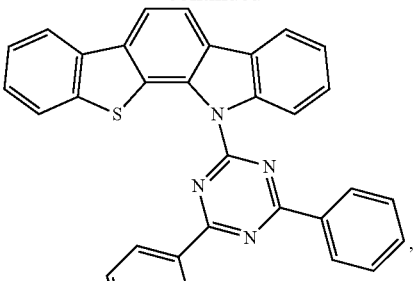
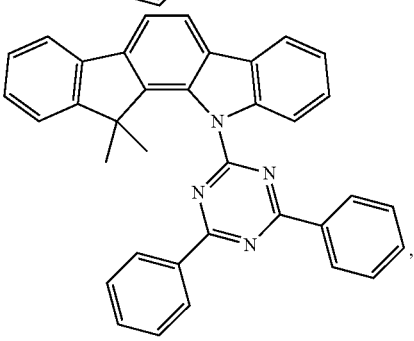
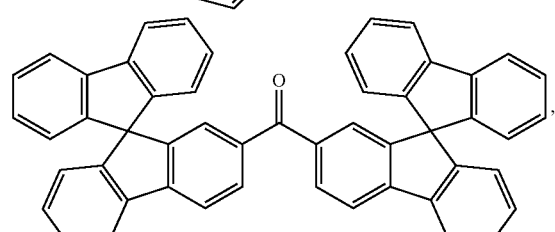
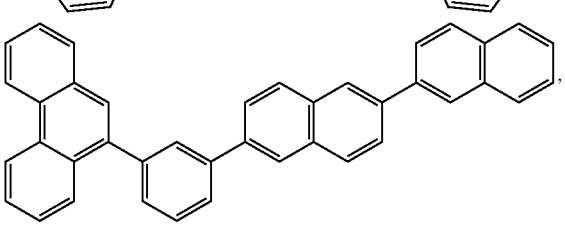
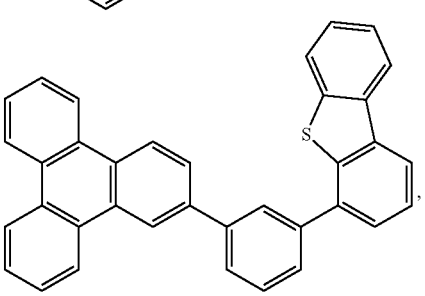
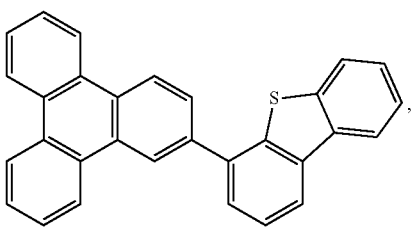 [SMILES: c1ccc2c(c1)sc1c(-c3ccc4c5ccccc5c5ccccc5c4c3)cccc12]
and combinations thereof.
In yet another embodiment, the host material comprises a metal complex.

According to another aspect of the present disclosure, a novel formulation is disclosed. The formulation comprises a compound which is an osmium(IV) complex having the formula Os(L)n is disclosed; wherein Os is osmium(IV) metal, L is a ligand coordinating to the Os atom, and n is an integer from 1 to 6; wherein each L can be same or different; wherein at least one L is a multidentate ligand; and wherein the compound is neutral.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

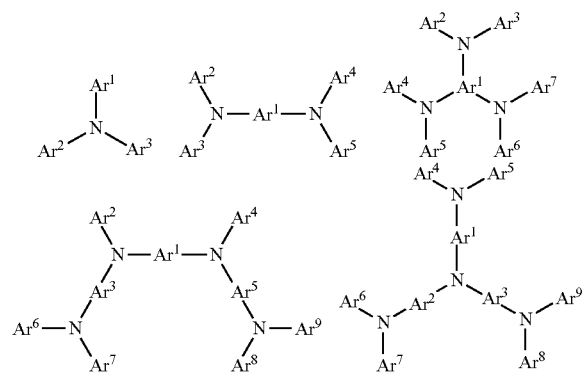

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

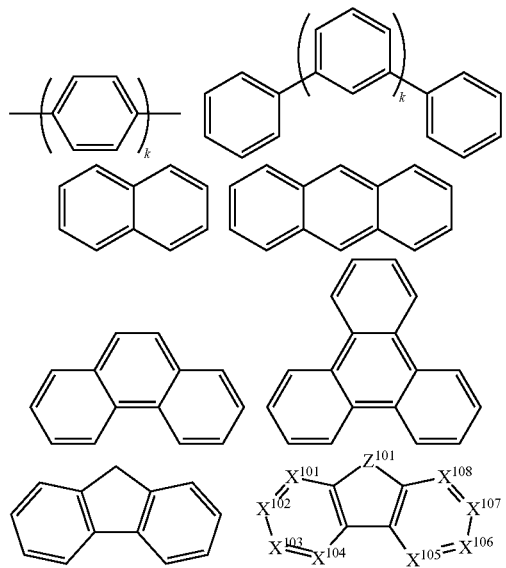

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

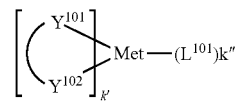

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}-Y^{102})$ is a 2-phenylpyridine derivative. In another aspect, $(Y^{101}-Y^{102})$ is a carbene ligand. In another aspect, Met is selected from Ir, Pt, Os, and Zn. In a further aspect, the metal complex has a smallest oxidation potential in solution vs. Fc$^+$/Fc couple less than about 0.6 V. Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

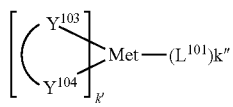

wherein Met is a metal; $(Y^{103}-Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

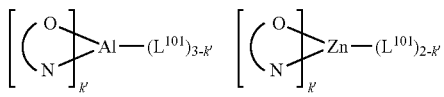

wherein (O—N) is a bidentate ligand, having metal coordinated to atoms O and N.

In another aspect, Met is selected from Ir and Pt. In a further aspect, $(Y^{103}-Y^{104})$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

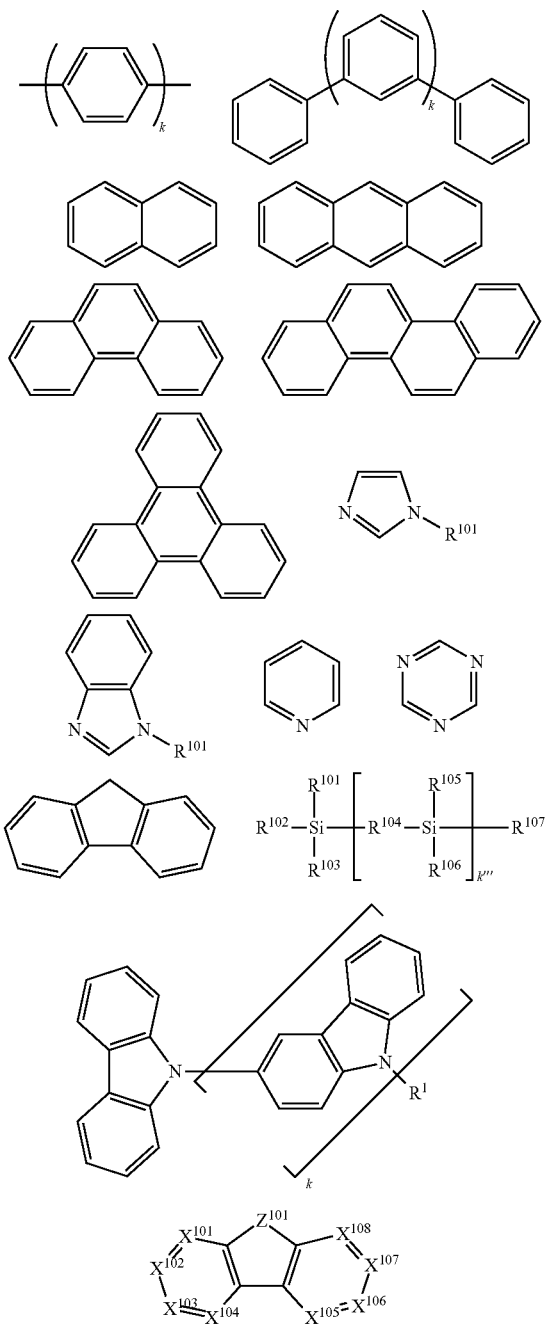

-continued

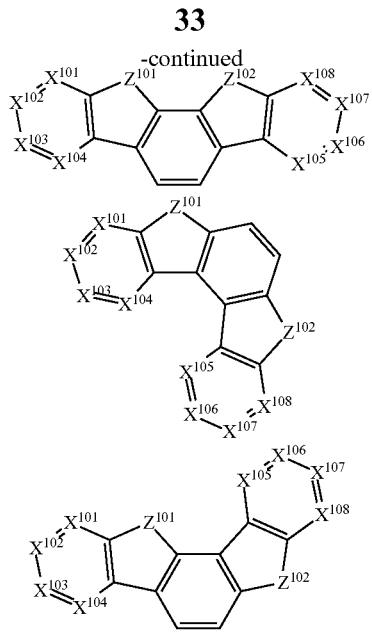

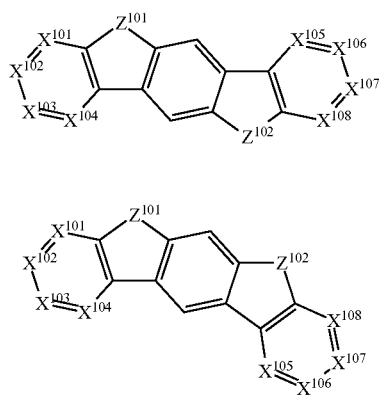

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

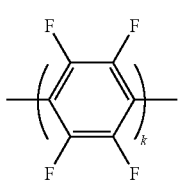 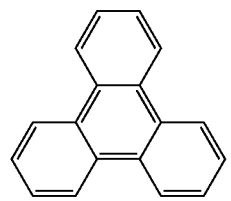

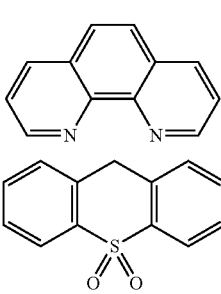 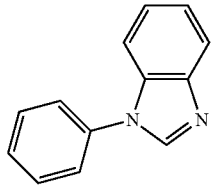

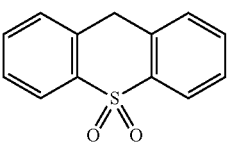 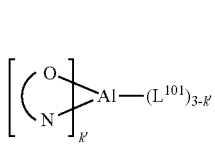

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

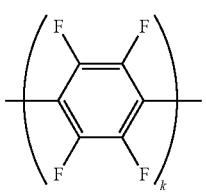 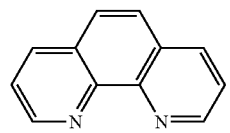

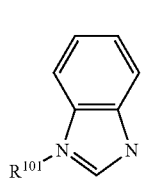 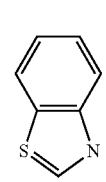 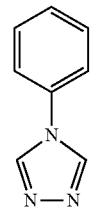

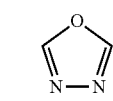 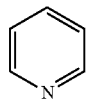 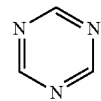

-continued

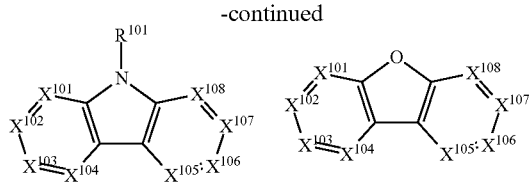

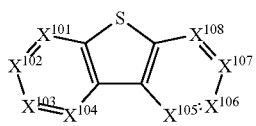

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

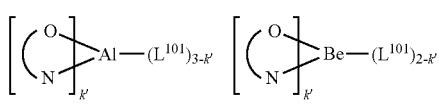

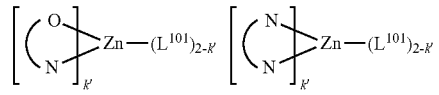

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| | Hole injection materials | |
| Phthalocyanine and porphryin compounds | | Appl. Phys. Lett. 69, 2160 (1996) |

TABLE 1-continued

| MATERIAL | EXAMPLES OF MATERIAL | PUBLICATIONS |
|---|---|---|
| Starburst triarylamines | | J. Lumin. 72-74, 985 (1997) |
| $CF_x$ Fluorohydrocarbon polymer | $-\!\!+\!\!CH_xF_y\!\!+\!\!_n$ | Appl. Phys. Lett. 78, 673 (2001) |
| Conducting polymers (e.g., PEDOT:PSS, polyaniline, polypthiophene) | | Synth. Met. 87, 171 (1997) WO 2007002683 |
| Phosphonic acid and silane SAMs | | US 20030162053 |
| Triarylamine or polythiophene polymers with conductivity dopants | | EP1725079A1 | and

TABLE 1-continued
| MATERIAL | EXAMPLES OF MATERIAL | PUBLICATIONS |
|---|---|---|
| | 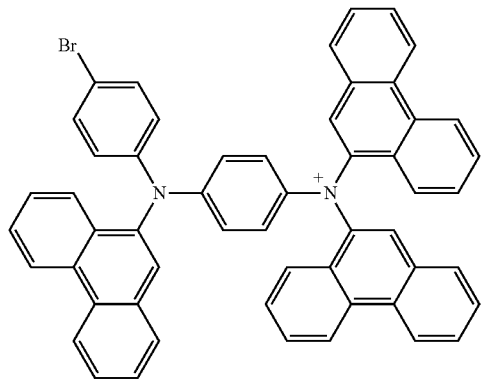 [SMILES: Brc1ccc(N(c2ccc(N(c3cc4ccccc4c4ccccc34)c3cc4ccccc4c4ccccc34)cc2)c2cc3ccccc3c3ccccc23)cc1] | |
| | 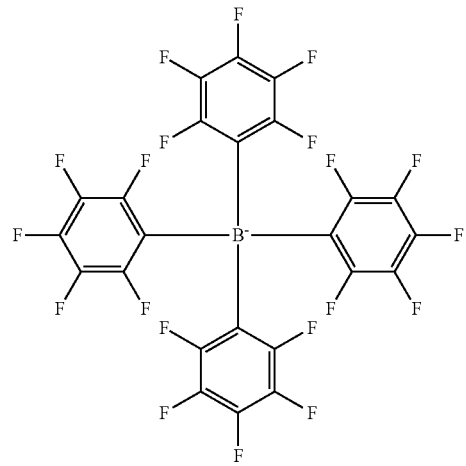 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Organic compounds with conductive inorganic compounds, such as molybdenum and tungsten oxides | 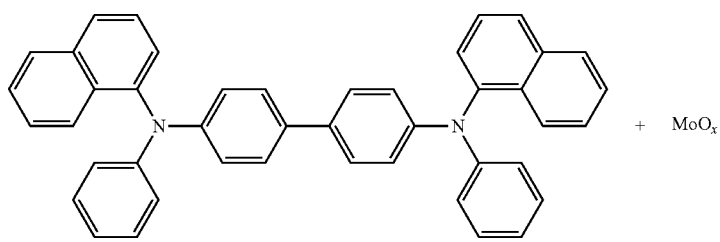 [SMILES: c1ccc(N(c2ccc(-c3ccc(N(c4ccccc4)c4cccc5ccccc45)cc3)cc2)c2cccc3ccccc23)cc1] + MoO$_x$ | US 20050123751 SID Symposium Digest, 37, 923 (2006) WO 2009018009 |
| n-type semiconducting organic complexes | 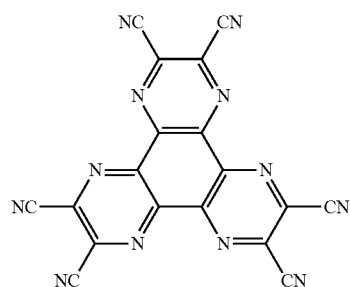 [SMILES: N#Cc1nc2c3nc(C#N)c(C#N)nc3c3nc(C#N)c(C#N)nc3c2nc1C#N] | US 20020158242 |

TABLE 1-continued

| MATERIAL | EXAMPLES OF MATERIAL | PUBLICATIONS |
|---|---|---|
| Metal organometallic complexes | | US 20060240279 |
| Crosslinkable compounds | | US 20080220265 |
| Polythiophene based polymers and copolymers | | WO 2011075644<br>EP2350216 |

Hole transporting materials

| | | |
|---|---|---|
| Triarylamines (e.g., TPD, α-NPD) | | Appl. Phys. Lett. 51, 913 (1987)<br>U.S. Pat. No. 5,061,569<br>EP650955 |

Hole injection materials

| | | |
|---|---|---|
| | | J. Mater. Chem. 3, 319 (1993) |

TABLE 1-continued
| MATERIAL | EXAMPLES OF MATERIAL | PUBLICATIONS |
|---|---|---|
| | 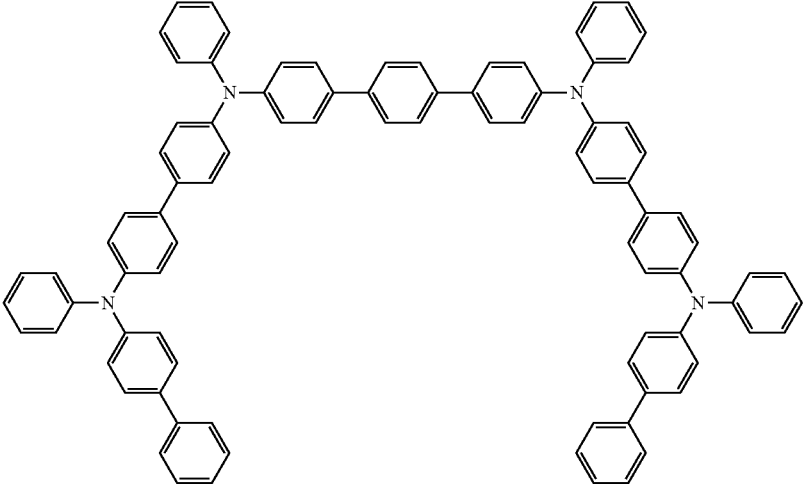 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |
| | 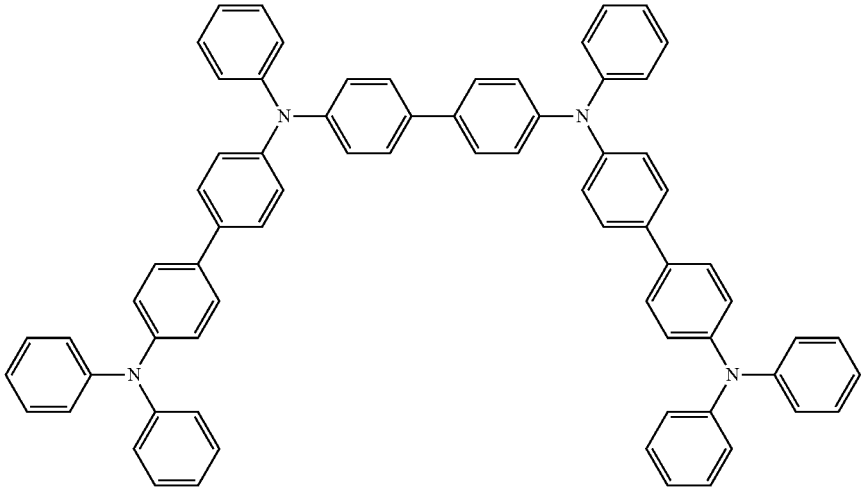 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triarylamine on spirofluorene core | 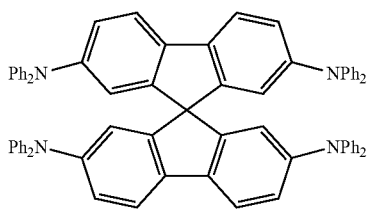 | Synth. Met. 91, 209 (1997) |

TABLE 1-continued

| MATERIAL | EXAMPLES OF MATERIAL | PUBLICATIONS |
|---|---|---|
| Arylamine carbazole compounds | | Adv. Mater. 6, 677 (1994), US 20080124572 |
| Triarylamine with (di)benzothiophene/ (di)benzofuran | | US 20070278938, US 20080106190 US 20110163302 |
| Indolocarbazoles | | Synth. Met. 111, 421 (2000) |
| Isoindole compounds | | Chem. Mater. 15, 3148 (2003) |

TABLE 1-continued

| MATERIAL | EXAMPLES OF MATERIAL | PUBLICATIONS |
|---|---|---|
| Metal carbene complexes | | US 20080018221 |

Phosphorescent OLED host materials
Red hosts

| Arylcarbazoles | | Appl. Phys. Lett. 78, 1622 (2001) |
|---|---|---|
| Metal 8-hydroxyquinolates (e.g., Alq$_3$, BAlq) | | Nature 395, 151 (1998) |
| | | US 20060202194 |
| | | WO 2005014551 |
| | | WO 2006072002 |

TABLE 1-continued

| MATERIAL | EXAMPLES OF MATERIAL | PUBLICATIONS |
|---|---|---|
| Hole injection materials | | |
| Metal phenoxy-benzothiazole compounds | | Appl. Phys. Lett. 90, 123509 (2007) |
| Conjugated oligomers and polymers (e.g., polyfluorene) | | Org. Electron. 1, 15, (2000) |
| Aromatic fused rings | | WO 2009066779, WO 2009066778, WO 2009063833, US 20090045731, US 20090045730, WO 2009008311, US 20090008605, US 20090009065 |
| Zinc complexes | | WO 2010056066 |
| Chrysene based compounds | | WO 2011086863 |

TABLE 1-continued

| MATERIAL | EXAMPLES OF MATERIAL | PUBLICATIONS |
|---|---|---|
| | Green hosts | |
| Arylcarbazoles | | Appl. Phys. Lett. 78, 1622 (2001) |
| | | US 20030175553 |
| | | WO 2001039234 |
| | Hole injection materials | |
| Aryltriphenylene compounds | | US 20060280965 |
| | | US 20060280965 |

TABLE 1-continued
| MATERIAL | EXAMPLES OF MATERIAL | PUBLICATIONS |
|---|---|---|
| | 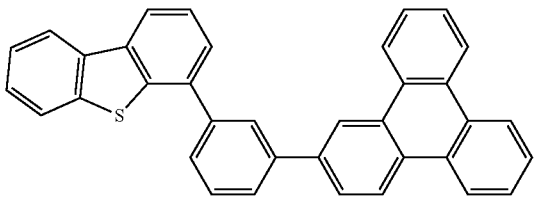 [SMILES: c1cc(-c2ccc3c4ccccc4c4ccccc4c3c2)cc(-c2cccc3c2sc2ccccc23)c1] | WO 2009021126 |
| Poly-fused heteroaryl compounds | 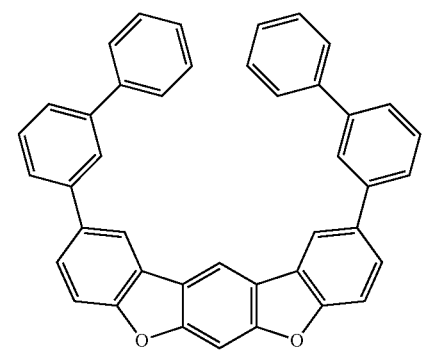 [SMILES: c1ccc(-c2cccc(-c3ccc4oc5cc6oc7ccc(-c8cccc(-c9ccccc9)c8)cc7c6cc5c4c3)c2)cc1] | US 20090309488 US 20090302743 US 20100012931 |
| Donor acceptor type molecules | 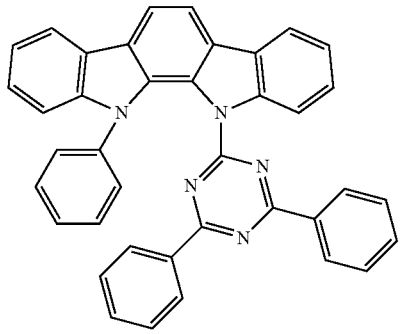 [SMILES: c1ccc(-c2nc(-c3ccccc3)nc(-n3c4ccccc4c4ccc5c6ccccc6n(-c6ccccc6)c5c43)n2)cc1] | WO 2008056746 |
| | 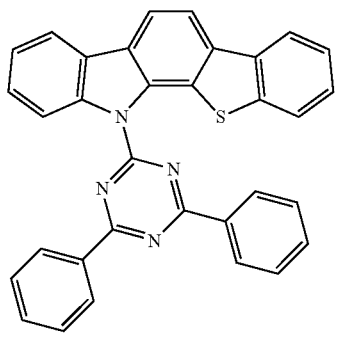 [SMILES: c1ccc(-c2nc(-c3ccccc3)nc(-n3c4ccccc4c4ccc5c6ccccc6sc5c43)n2)cc1] | WO 2010107244 |

TABLE 1-continued
| MATERIAL | EXAMPLES OF MATERIAL | PUBLICATIONS |
|---|---|---|
| Aza-carbazole/ DBT/DBF | 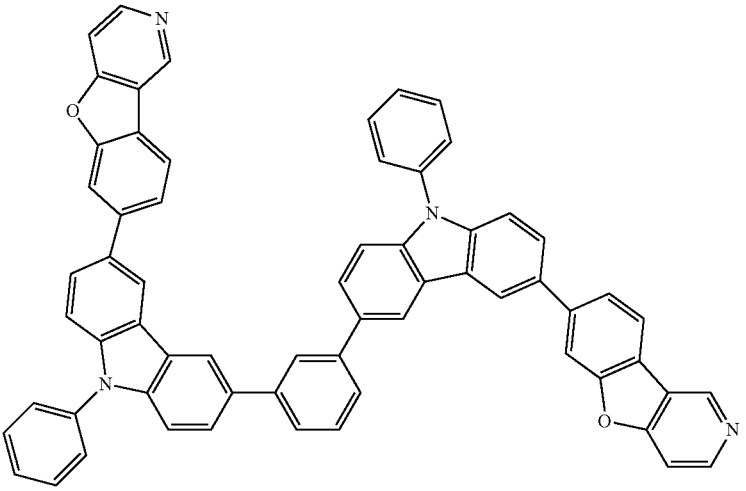 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 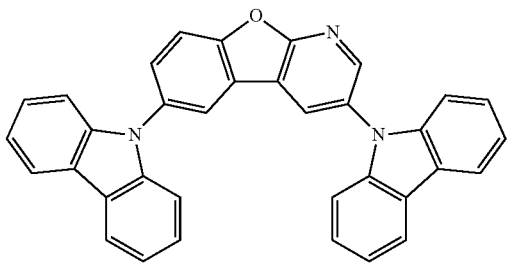 [SMILES: c1ccc2c(c1)c1ccccc1n2-c1ccc2oc3ncc(-n4c5ccccc5c5ccccc54)cc3c2c1] | US 20100187984 |
| Polymers (e.g., PVK) | 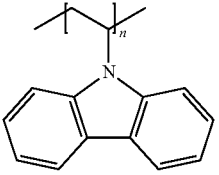 | Appl. Phys. Lett. 77, 2280 (2000) |
| Spiro-fluorene compounds | 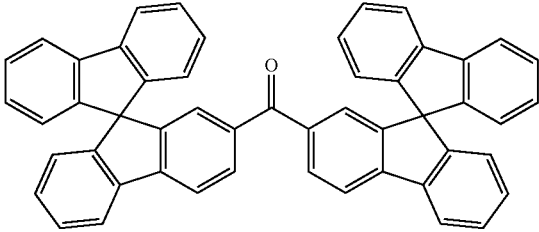 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO 2004093207 |
| Metal phenoxy-benzo-oxazole compounds | 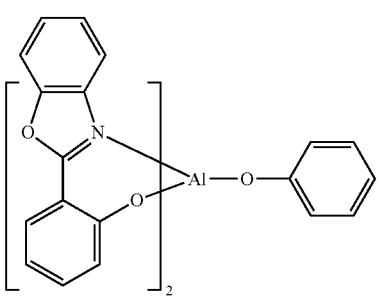 | WO 2005089025 |

TABLE 1-continued

| MATERIAL | EXAMPLES OF MATERIAL | PUBLICATIONS |
|---|---|---|
| | | WO 2006132173 |
| | | JP200511610 |
| Spiro-fluorene-carbazole compounds | | JP2007254297 |
| | | JP2007254297 |
| Indolocabazoles | | WO 2007063796 |

TABLE 1-continued
| MATERIAL | EXAMPLES OF MATERIAL | PUBLICATIONS |
|---|---|---|
| | 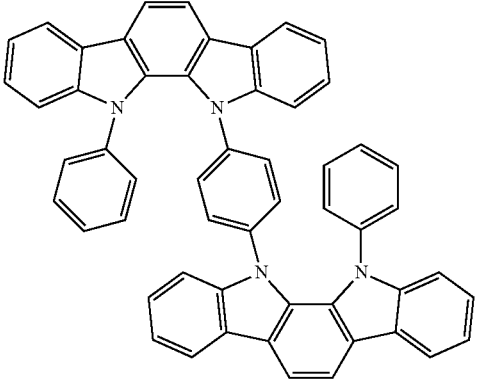 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO 2007063754 |
| 5-member ring electron deficient heterocycles (e.g., triazole, oxadiazole) | 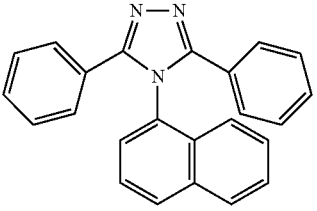 [SMILES: c1ccc(-c2nnc(-c3ccccc3)n2-c2cccc3ccccc23)cc1] | J. Appl. Phys. 90, 5048 (2001) |
| | 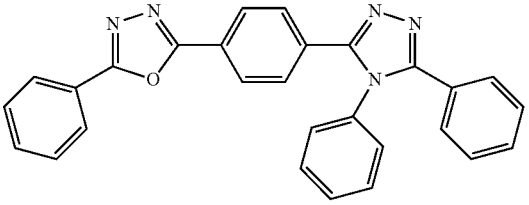 [SMILES: c1ccc(-c2nnc(-c3ccc(-c4nnc(-c5ccccc5)n4-c4ccccc4)cc3)o2)cc1] | WO 2004107822 |
| Tetraphenylene complexes | 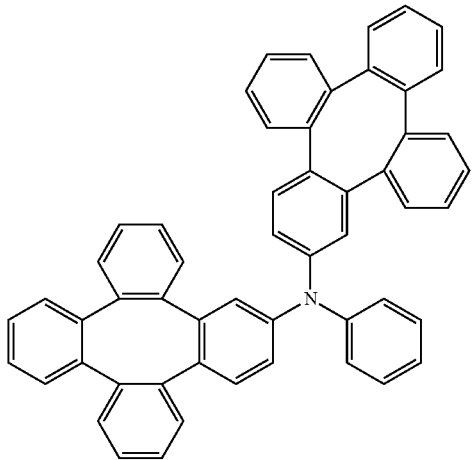 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US 20050112407 |
| Metal phenoxypyridine compounds | 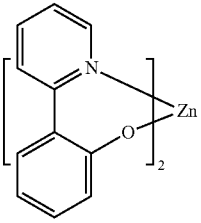 | WO 2005030900 |

TABLE 1-continued

| MATERIAL | EXAMPLES OF MATERIAL | PUBLICATIONS |
|---|---|---|
| Metal coordination complexes (e.g., Zn, Al with N^N ligands) | | US 20040137268, US 20040137267 |И
| | Blue hosts | |
| Arylcarbazoles | | Appl. Phys. Lett, 82, 2422 (2003) |
| | | US 20070190359 |
| Dibenzothiophene/ Dibenzofuran-carbazole compounds | | WO 2006114966, US 20090167162 |
| | | US 20090167162 |
| | | WO 2009086028 |

TABLE 1-continued
| MATERIAL | EXAMPLES OF MATERIAL | PUBLICATIONS |
|---|---|---|
| | 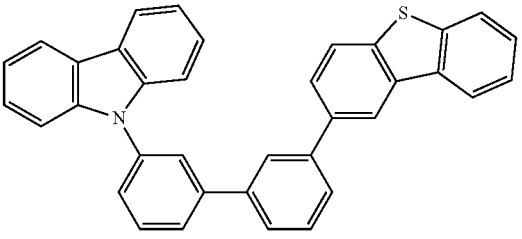 [SMILES: c1cc(-c2cccc(-n3c4ccccc4c4ccccc43)c2)cc(-c2ccc3sc4ccccc4c3c2)c1] | US 20090030202, US 20090017330 |
| | 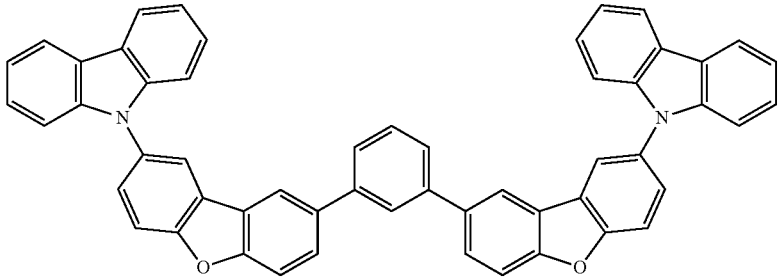 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US 20100084966 |
| Hole injection materials | | |
| Silicon aryl compounds | 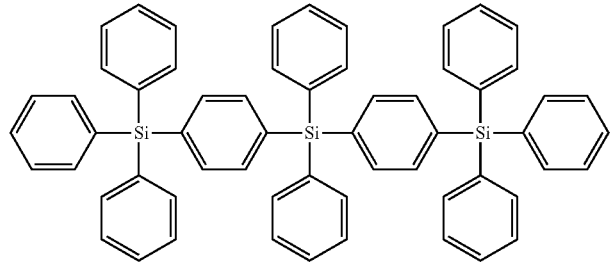 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US 20050238919 |
| | 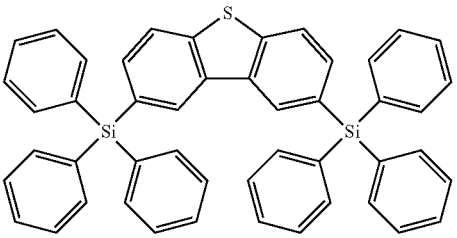 [SMILES: c1ccc([Si](c2ccccc2)(c2ccccc2)c2ccc3sc4ccc([Si](c5ccccc5)(c5ccccc5)c5ccccc5)cc4c3c2)cc1] | WO 2009003898 |
| Silicon/ Germanium aryl compounds | 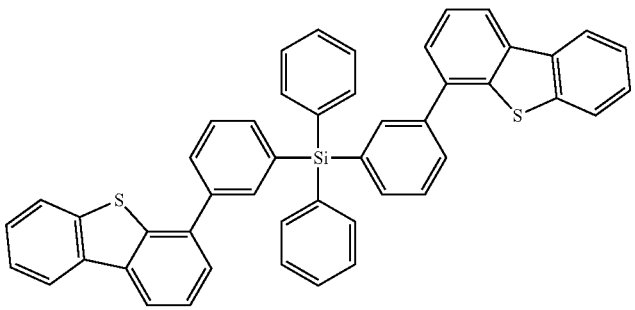 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |

TABLE 1-continued

| MATERIAL | EXAMPLES OF MATERIAL | PUBLICATIONS |
|---|---|---|
| Aryl benzoyl ester | | WO 200100298 |
| Carbazole linked by non-conjugated groups | | US 20040115476 |
| Aza-carbazoles | | US 20060121308 |
| High triplet metal organo-metallic complex | | U.S. Pat. No. 7,154,114 |

Phophorescent dopants
Hole injection materials
Red dopants

| | | |
|---|---|---|
| Heavy metal porphyrins (e.g., PtOEP) | | Nature 395, 151 (1998) |

TABLE 1-continued
| MATERIAL | EXAMPLES OF MATERIAL | PUBLICATIONS |
|---|---|---|
| Iridium(III) organometallic complexes | 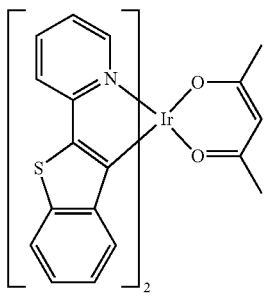 | Appl. Phys. Lett. 78, 1622 (2001) |
| | 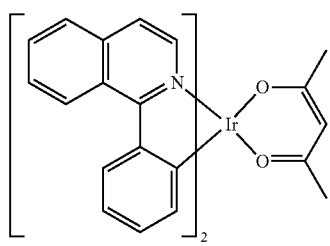 | US 2006835469 |
| | 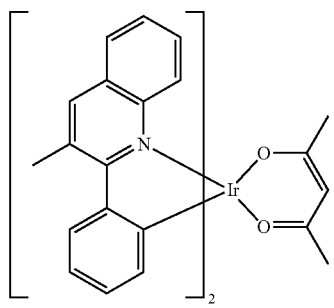 | US 2006835469 |
| | 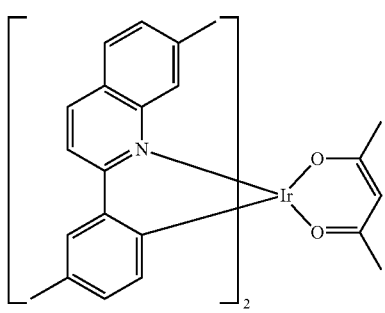 | US 20060202194 |
| | 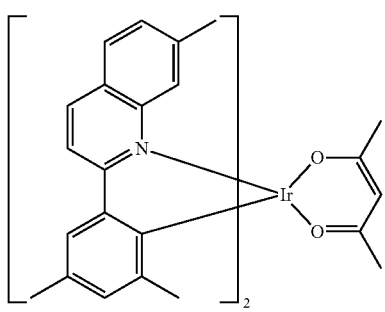 | US 20060202194 |

TABLE 1-continued

| MATERIAL | EXAMPLES OF MATERIAL | PUBLICATIONS |
|---|---|---|
| | | US 20070087321 |
| | | US 20080261076 US 20100090591 |
| | | US 20070087321 |
| | | Adv. Mater. 19, 739 (2007) |
| | | WO 2009100991 |

TABLE 1-continued

| MATERIAL | EXAMPLES OF MATERIAL | PUBLICATIONS |
|---|---|---|
| | | WO 2008101842 |
| | | U.S. Pat. No. 7,232,618 |
| Platinum (II) organometallic complexes | | WO 2003040257 |
| | | US 20070103060 |
| Osminium (III) complexes | | Chem. Mater. 17, 3532 (2005) |

TABLE 1-continued

| MATERIAL | EXAMPLES OF MATERIAL | PUBLICATIONS |
|---|---|---|
| Ruthenium (II) complexes | | Adv. Mater. 17, 1059 (2005) |
| Rhenium (I), (II), and (III) complexes | | US 20050244673 |

Green dopants

| | | |
|---|---|---|
| Iridium (III) organometallic complexes | and its derivatives | Inorg. Chem. 40, 1704 (2001) |
| | | US 20020034656 |

TABLE 1-continued
| MATERIAL | EXAMPLES OF MATERIAL | PUBLICATIONS |
|---|---|---|
| | 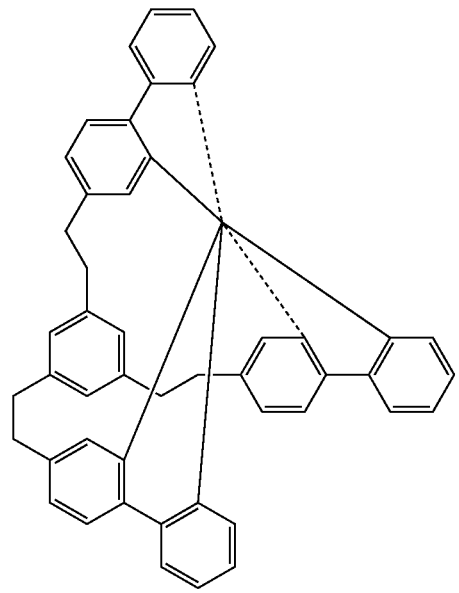 | U.S. Pat. No. 7,332,232 |
| Hole injection materials | | |
| | 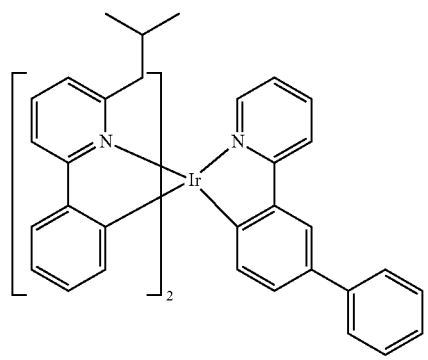 | US 20090108737 |
| | 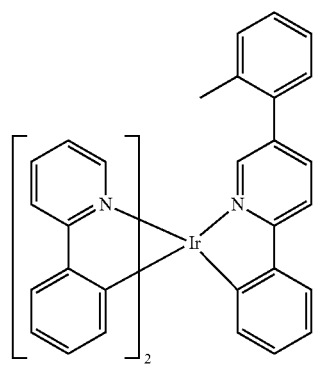 | WO 2010028151 |

TABLE 1-continued
| MATERIAL | EXAMPLES OF MATERIAL | PUBLICATIONS |
|---|---|---|
| | 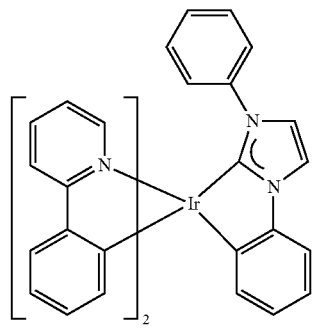 | EP1841834B |
| | 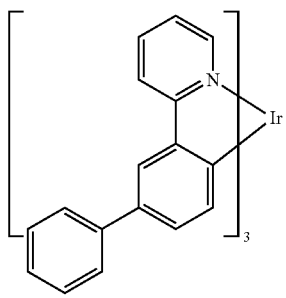 | US 20060127696 |
| | 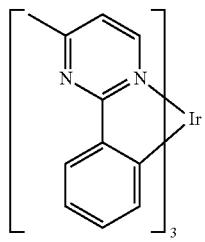 | US 20090039776 |
| | 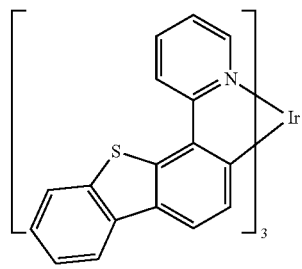 | U.S. Pat. No. 6,921,915 |
| | 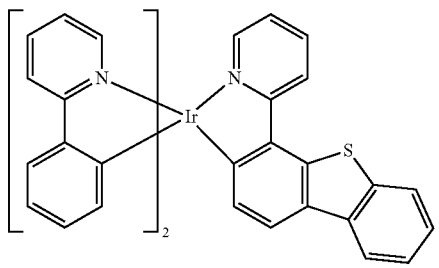 | US 20100244004 |

TABLE 1-continued

| MATERIAL | EXAMPLES OF MATERIAL | PUBLICATIONS |
|---|---|---|
| | | U.S. Pat. No. 6,687,266 |
| | | Chem. Mater. 16, 2480 (2004) |
| | | US 20070190359 |
| | | US 20060008670 JP2007123392 |
| | | WO 2010086089, WO 2011044988 |
| | | Adv. Mater. 16, 2003 (2004) |

TABLE 1-continued
| MATERIAL | EXAMPLES OF MATERIAL | PUBLICATIONS |
|---|---|---|
| | 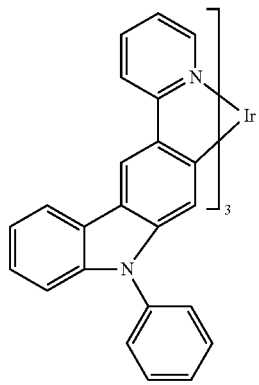 | Angew. Chem. Int. Ed. 2006, 45, 7800 |
| | 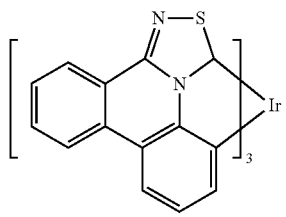 | WO 2009050290 |
| | 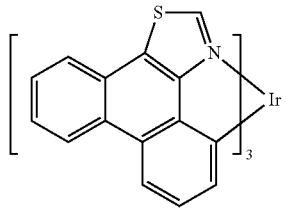 | WO 20090165846 |
| | 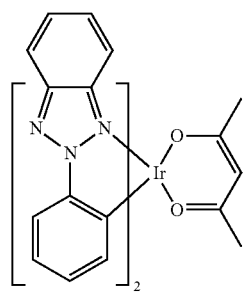 | US 20080015355 |
| | 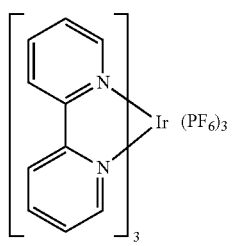 | US 20010015432 |

TABLE 1-continued

| MATERIAL | EXAMPLES OF MATERIAL | PUBLICATIONS |
|---|---|---|
|  | [structure] | US 20100295032 |
| Monomer for polymeric metal organometallic compounds | [structure] | U.S. Pat. No. 7,250,226, U.S. Pat. No. 7,396,598 |
| Pt(II) organometallic complexes, including polydentated ligands | [structure] | Appl. Phys. Lett. 86, 153505 (2005) |
|  | [structure] | Appl. Phys. Lett. 86, 153505 (2005) |
|  | [structure] | Chem. Lett. 34, 592 (2005) |

| MATERIAL | EXAMPLES OF MATERIAL | PUBLICATIONS |
|---|---|---|
| | 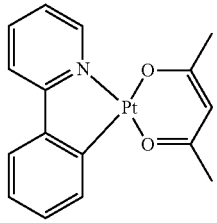 | WO 2002015645 |
| | 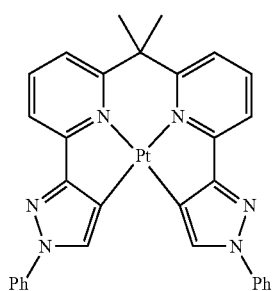 | US 20060263635 |
| | 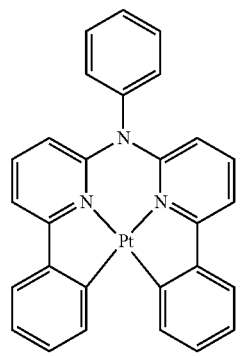 | US 20060182992<br>US 20070103060 |
| Cu complexes | 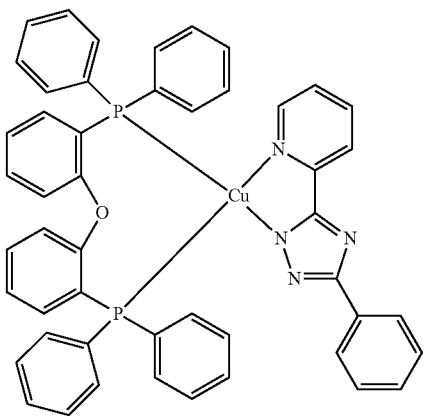 | WO 2009000673 |

TABLE 1-continued

| MATERIAL | EXAMPLES OF MATERIAL | PUBLICATIONS |
|---|---|---|
| | | US 20070111026 |
| Gold complexes | | Chem. Commun. 2906 (2005) |
| Rhenium (III) complexes | | Inorg. Chem. 42, 1248 (2003) |
| Osmium(II) complexes | | U.S. Pat. No. 7,279,704 |

TABLE 1-continued

| MATERIAL | EXAMPLES OF MATERIAL | PUBLICATIONS |
|---|---|---|
| Deuterated organometallic complexes | | US 20030138657 |
| Organometallic complexes with two or more metal centers | | US 20030152802 |
| | | U.S. Pat. No. 7,090,928 |

Blue dopants

| | | |
|---|---|---|
| Iridium(III) organometallic complexes | | WO 2002002714 |

TABLE 1-continued
| MATERIAL | EXAMPLES OF MATERIAL | PUBLICATIONS |
|---|---|---|
| | 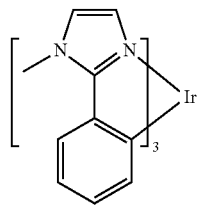 | WO 2006009024 |
| Hole injection materials | | |
| | 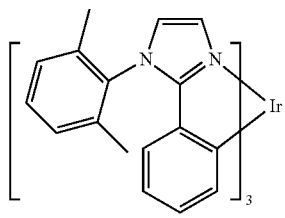 | US 2006251923 US 20110057559 US 20110204333 |
| | 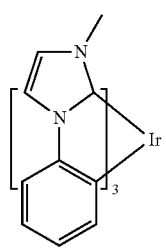 | U.S. Pat. No. 7,393,599, WO 2006056418, US 20050260441, WO 2005019373 |
| | 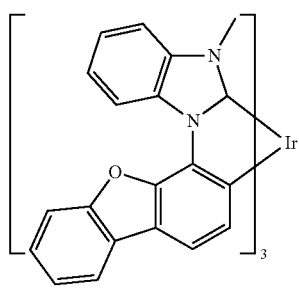 | U.S. Pat. No. 7,534,505 |
| | 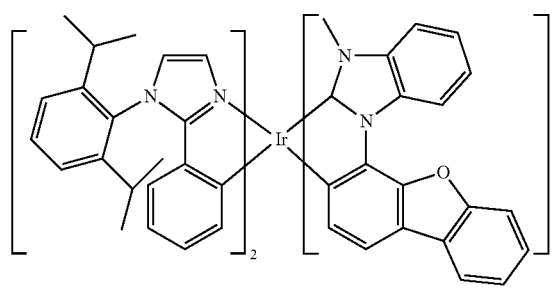 | WO 2011051404 |

TABLE 1-continued
| MATERIAL | EXAMPLES OF MATERIAL | PUBLICATIONS |
|---|---|---|
| | 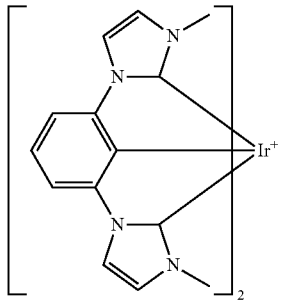 | U.S. Pat. No. 7,445,855 |
| | 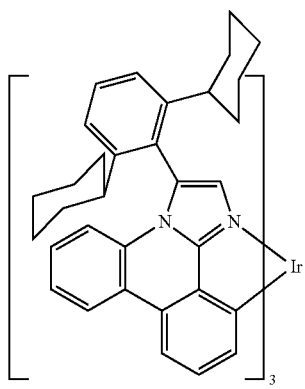 | US 20070190359, US 20080297033 US 20100148663 |
| | 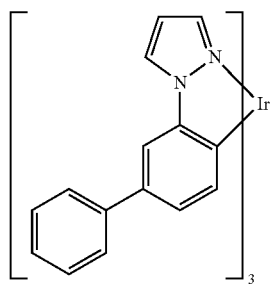 | U.S. Pat. No. 7,338,722 |
| | 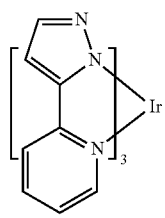 | US 20020134984 |
| | 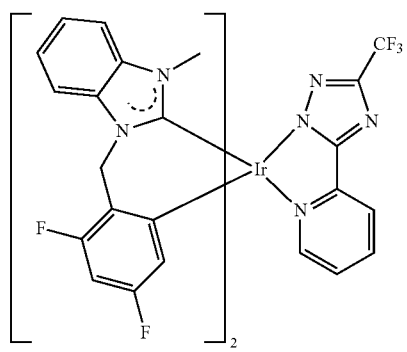 | Angew. Chem. Int. Ed. 47, 4542 (2008) |

| MATERIAL | EXAMPLES OF MATERIAL | PUBLICATIONS |
|---|---|---|
| | 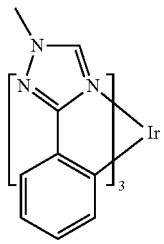 | Chem. Mater. 18, 5119 (2006) |
| | 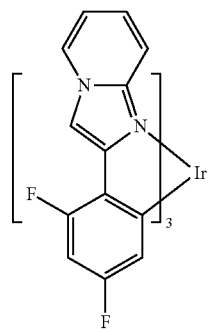 | Inorg. Chem. 46, 4308 (2007) |
| | 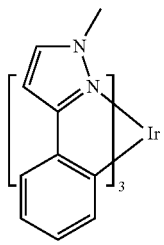 | WO 2005123873 |
| | 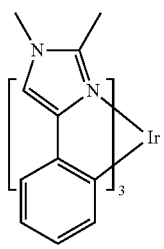 | WO 2005123873 |
| | 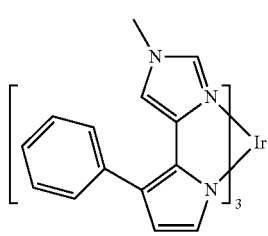 | WO 2007004380 |

TABLE 1-continued

| MATERIAL | EXAMPLES OF MATERIAL | PUBLICATIONS |
|---|---|---|
| | | WO 2006082742 |
| Osmium (II) complexes | | U.S. Pat. No. 7,279,704 |
| | | Organometallics 23, 3745 (2004) |
| Gold complexes | | Appl. Phys. Lett. 74, 1361 (1999) |
| Platinum (II) complexes | | WO 2006098120, WO 2006103874 |

TABLE 1-continued

| MA-TERIAL | EXAMPLES OF MATERIAL | PUBLICATIONS |
|---|---|---|
| Pt tetradentate complexes with at least one metal-carbene bond | 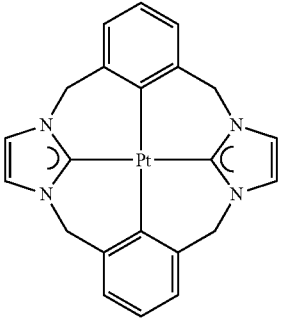 | U.S. Pat. No. 7,655,323 |

Exciton/hole blocking layer materials

| | | |
|---|---|---|
| Bathocuprine compounds (e.g., BCP, BPhen) | 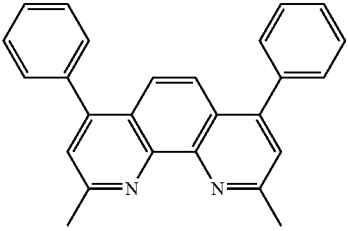 [SMILES: Cc1cc(-c2ccccc2)c2ccc3c(-c4ccccc4)cc(C)nc3c2n1] | Appl. Phys. Lett. 75, 4 (1999) |
| | | Appl. Phys. Lett. 79, 449 (2001) |

Hole injection materials

| | | |
|---|---|---|
| Metal 8-hydroxyquinolates (e.g., BAlq) | 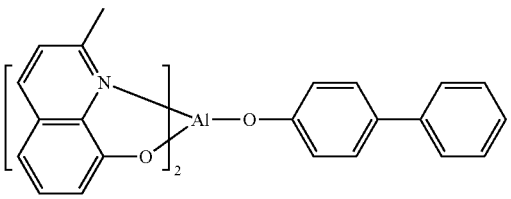 | Appl. Phys. Lett. 81, 162 (2002) |
| 5-member ring electron deficient heterocycles such as triazole, oxadiazole, imidazole, benzoimidazole | 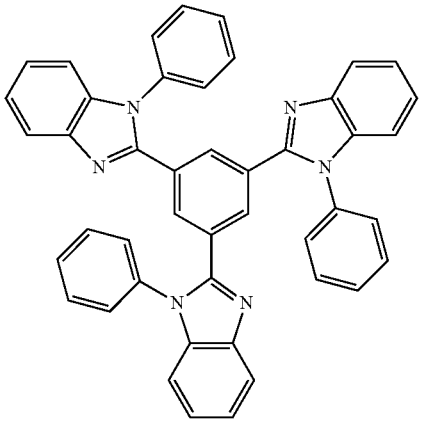 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 1-continued

| MATERIAL | EXAMPLES OF MATERIAL | PUBLICATIONS |
|---|---|---|
| Triphenylene compounds | | US 20050025993 |
| Fluorinated aromatic compounds | | Appl. Phys. Lett. 79, 156 (2001) |
| Phenothiazine-S-oxide | | WO 2008132085 |
| Silylated five-membered nitrogen, oxygen, sulfur or phosphorus dibenzo-heterocycles | | WO 2010079051 |

TABLE 1-continued
| MATERIAL | EXAMPLES OF MATERIAL | PUBLICATIONS |
|---|---|---|
| Aza-carbazoles | 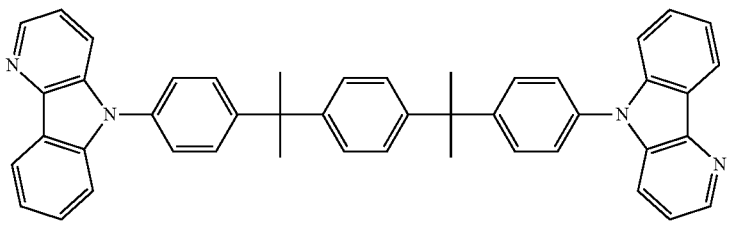 [SMILES: CC(C)(c1ccc(-n2c3ccccc3c3ncccc32)cc1)c1ccc(C(C)(C)c2ccc(-n3c4ccccc4c4ncccc43)cc2)cc1] | US 20060121308 |
Electron transporting materials
| | | |
|---|---|---|
| Anthracene-benzo-imidazole compounds | 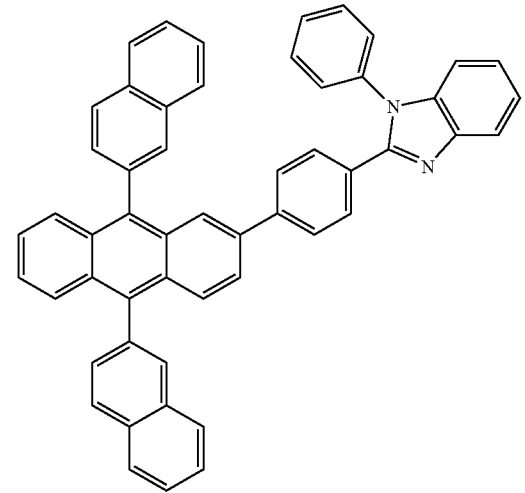 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO 2003060956 |
| | 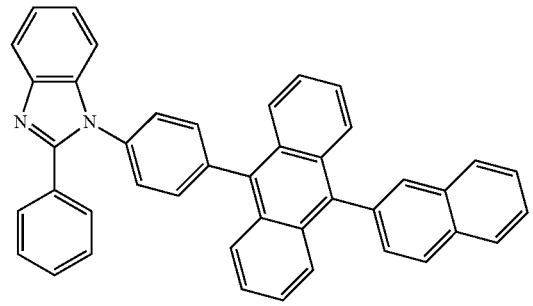 [SMILES: c1ccc(-c2nc3ccccc3n2-c2ccc(-c3c4ccccc4c(-c4ccc5ccccc5c4)c4ccccc34)cc2)cc1] | US 20090179554 |
| Aza triphenylene derivatives | 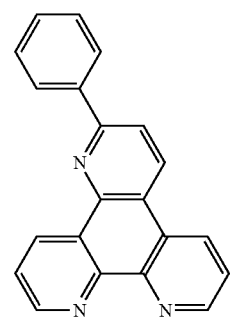 [SMILES: c1ccc(-c2ccc3c4cccnc4c4ncccc4c3n2)cc1] | US 20090115316 |

TABLE 1-continued

| MATERIAL | EXAMPLES OF MATERIAL | PUBLICATIONS |
|---|---|---|
| Anthracene-benzothiazole compounds | | Appl. Phys. Lett. 89, 063504 (2006) |
| Metal 8-hydroxyquinolates (e.g., Alq$_3$, Zrq$_4$) | | Appl. Phys. Lett. 51, 913 (1987) U.S. Pat. No. 7,230,107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| Hole injection materials | | |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |

TABLE 1-continued
| MATERIAL | EXAMPLES OF MATERIAL | PUBLICATIONS |
|---|---|---|
| | 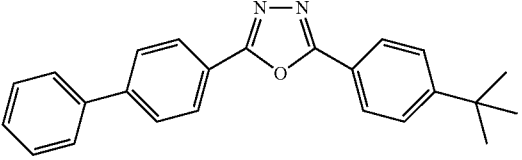 [SMILES: CC(C)(C)c1ccc(-c2nnc(-c3ccc(-c4ccccc4)cc3)o2)cc1] | Appl. Phys. Lett. 55, 1489 (1989) |
| | 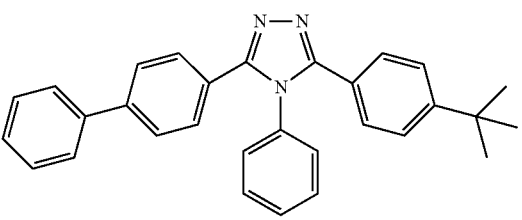 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 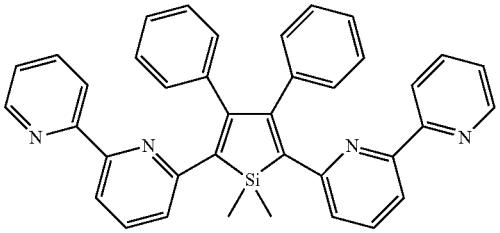 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 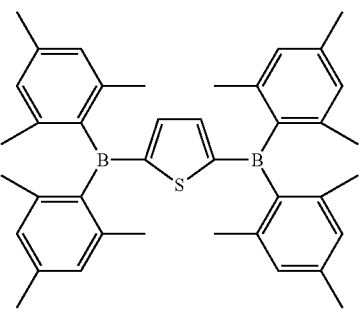 | J. Am. Chem. Soc. 120, 9714 (1998) |
| Fluorinated aromatic compounds | 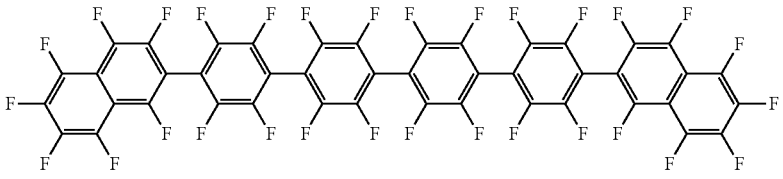 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 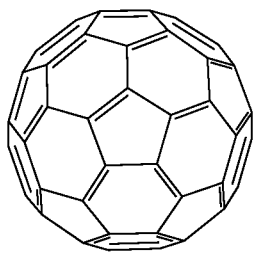 [SMILES: c1cc2c3ccc4c5ccc6c7ccc8c9ccc%10c1c1c2c2c3c4c3c5c6c4c7c8c5c9c%10c1c1c2c3c4c51] | US 20090101870 |

TABLE 1-continued

| MA-TERIAL | EXAMPLES OF MATERIAL | PUBLICATIONS |
|---|---|---|
| Triazine complexes | | US 20040036077 |
| Zn (N^N) complexes | | U.S. Pat. No. 6,528,187 |

Experimental Verification

All reactions were carried out with rigorous exclusion of air using Schlenk-tube techniques. Solvents, except acetonitrile that was dried and distilled under argon, were obtained oxygen-free and water-free from an MBraun solvent purification apparatus. $^1$H, $^{31}$P{$^1$H}, $^{19}$F and $^{13}$C{$^1$H} NMR spectra were recorded on Bruker 300 ARX, Bruker Avance 300 MHz, and Bruker Avance 400 MHz instruments. Chemical shifts, expressed in parts per million, are referenced to residual solvent peaks ($^1$H, $^{13}$C{$^1$H}) or external 85% H$_3$PO$_4$ ($^{31}$P{$^1$H}), or external CFCl$_3$ ($^{19}$F). Coupling constants J and N are given in hertz. Attenuated total reflection infrared spectra (ATR-IR) of solid samples were run on a Perkin-Elmer Spectrum 100 FT-IR spectrometer. C, H, and N analyses were carried out in a Perkin-Elmer 2400 CHNS/O analyzer. High-resolution electrospray mass spectra were acquired using a MicroTOF-Q hybrid quadrupole time-of-flight spectrometer (Bruker Daltonics, Bremen, Germany). OsH$_6$(P$^i$Pr$_3$)$_2$ was prepared by published method. (Inorganic Chemistry 1991, 30, 288-293)

Preparation of Trihydride-Bi2 (Compound V-1)

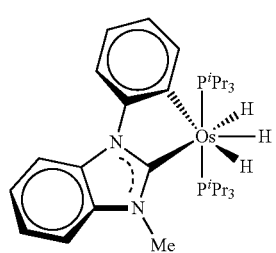

Toluene (40 mL) and NEt$_3$ (120 μl, 0.86 mmol) were added to a mixture of OsH$_6$(P$^i$Pr$_3$)$_2$ (400 mg, 0.78 mmol) and 1-phenyl-3-methyl-1-H-benzimidazolium tetrafluoroborate (Bi2, 229.2 mg, 0.78 mmol). The resulting mixture was refluxed for 4 hours and then the brownish-yellow solution was extracted and concentrated under vacuum to 1 mL. MeOH was added (8 mL), affording a white powder which was filtered and washed with MeOH (2×4 mL) at 195 K and dried in vacuo. Yield: 76.4% 426.0 mg. Anal. Calcd.

for C$_{32}$H$_{56}$N$_2$OsP$_2$: C, 53.31%; H, 7.83%; N, 3.89%. Found: C, 53.01%; H, 8.14%; N, 3.91%. HRMS (electrospray, m/z): calcd for C$_{32}$H$_{51}$N$_2$OsP$_2$[M-5H]$^+$: 719.3295. found: 719.3281. IR (cm$^{-1}$): ν(Os—H) 2044 (m).

Figure 3:
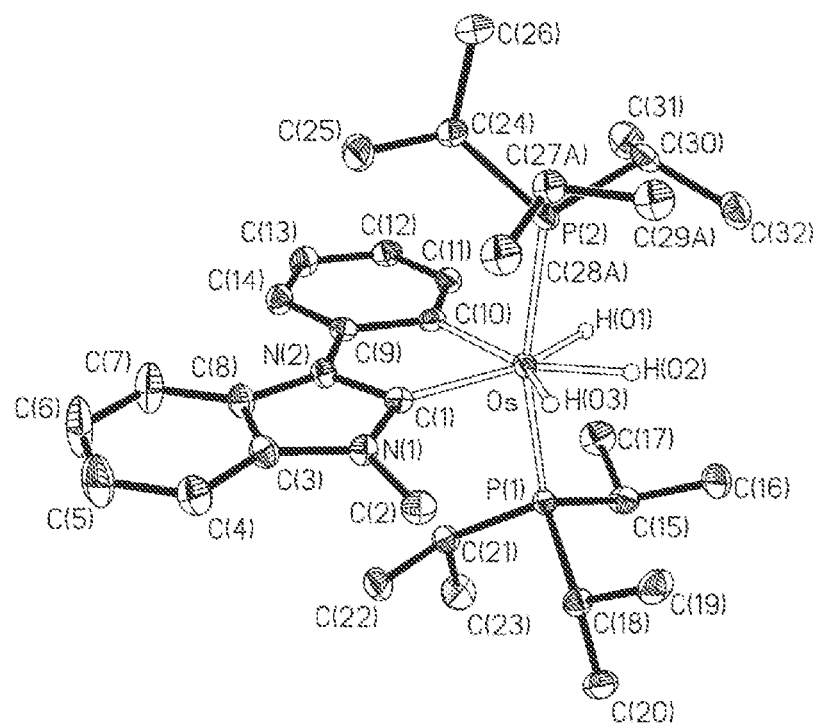
FIG. 3 shows a Molecular structure of complex trihydride.

$^1$H NMR (400 MHz, C$_6$D$_6$, 293 K): δ 8.66 (d, J$_{H—H}$=7.2, 1H, CH Ph), 7.91-7.88 (m, 2H, CH Ph, CH Bzm), 7.24 (ddd, J$_{H—H}$=7.2, J$_{H—H}$=7.2, J$_{H—H}$=1.0, 1H, CH Ph), 7.10 (ddd, J$_{H—H}$=7.2, J$_{H—H}$=7.2, J$_{H—H}$=1.0, 1H, CH Ph), 7.05-6.99 (m, 2H, CH Bzm), 6.91 (m, 1H, CH Bzm), 3.92 (s, 3H, N—CH$_3$), 1.79 (m, 6H, PCH), 0.96 (dvt, N=12.5, J=6.9, 18H, PCH(CH$_3$)$_2$) 0.83 (dvt, N=12.5, J=6.9, 18H, PCH(CH$_3$)$_2$), -8.18 (br, 1H, Os—H), -9.94 (br, 2H, Os—H). T$_{1(min)}$ (ms, OsH, 400 MHz, CD$_2$Cl$_2$): 118.2±10 (213 K). $^{13}$C {$^1$H}-APT NMR, HMBC and HSQC (100.6 MHz, C$_6$D$_6$, 293 K): δ 206.3 (t, J$_{C—P}$=5.4, NCN Bzm), 157.9 (t, J$_{C—P}$=6.7, Os—C Ph), 148.9 (s, N—C Ph), 148.0 (s, C—H Ph), 137.5 (s, C Bzm), 133.6 (s, C Bzm), 124.3 (s, C—H Ph), 122.1 (s, C—H Bzm), 121.3 (s, C—H Bzm), 119.8 (s, C—H Ph), 112.5 (s, C—H Bzm), 110.4 (s, C—H Ph), 109.1 (s, C—H Bzm), 36.6 (s, N—CH$_3$ Bzm), 27.9 (dvt, N=25.0, P—CH), 19.9 (s, PCH(CH$_3$)$_2$), 19.8 (s, PCH(CH$_3$)$_2$). $^{31}$P{$^1$H} NMR (162.0 MHz, C$_6$D$_6$, 293 K): δ 25.7 (s). FIG. 3 shows X-ray diffraction analysis of this complex, showing the molecular structure of the complex trihydride. Selected bond lengths (Å) and angles (°): Os—P(1)=2.3435(7), Os—P(2)=2.3538(7), Os—C(1)=2.069(2), Os—C(10)=2.140(3), H(01)-H(02)=1.69(3), H(01)-H(03)=1.74(3); P(1)-Os—P(2)=165.17(2), C(1)-Os—C(10)=75.69(9).

Preparation of Trihydride-Bi3 (Compound V-2)

Toluene (40 mL) and NEt$_3$ (120 μl, 0.86 mmol) were added to a mixture of OsH$_6$(P$^i$Pr$_3$)$_2$ (400 mg, 0.78 mmol) and 1-phenyl-3-methyl-1-H,-5,6-dimethyl-benzimidazolium tetrafluoroborate (Bi3, 250.9 mg, 0.78 mmol). The resulting mixture was refluxed for 4 hour and then the solution was extracted and concentrated under vacuum to 1 mL. MeOH was added (8 mL) and the resulting white powder was filtered and washed with MeOH (3×3 mL). Yield: 84% 490.7. Anal. Calcd. for C$_{34}$H$_{60}$N$_2$OsP$_2$·CH$_3$OH: C, 53.82%; H, 8.26%; N, 3.59%. Found: C, 53.99%; H, 8.51%; N, 3.67%. HRMS (electrospray, m/z): calcd for C$_{34}$H$_{55}$OsP$_2$N$_2$ [M-H]$^+$: 745.3452. found: 745.3460. IR: (cm$^{-1}$) ν(Os—H) 2049 (m), ν(Os—H) 2027 (m).

$^1$H NMR (400 MHz, C$_6$D$_6$, 293 K): δ 8.67 (d, J$_{H—H}$=7.5, 1H, CH Ph), 8.02 (dd, J$_{H—H}$=7.5, J$_{H—H}$=0.8, 1H, CH Ph), 7.88 (s, 1H, H Bzm), 7.24 (ddd, J$_{H—H}$=7.5, J$_{H—H}$=7.5, J$_{H—H}$=1.1, 1H, CH Ph), 7.10 (ddd, J$_{H—H}$=7.5, J$_{H—H}$=7.5, J$_{H—H}$=0.8, 1H, CH Ph), 6.80 (s, 1H, CH Bzm), 3.96 (s, 3H, N—CH$_3$), 2.13 and 2.12 (both s, each 3H, —CH$_3$ Bzm), 1.84 (m, 6H, P—CH), 0.99 (dvt, N=12.5, J=6.9, 18H, PCH(CH$_3$)$_2$), 0.87 (dvt, N=12.5, J=6.9, 18H, PCH(CH$_3$)$_2$), -8.21 (br, 1H, Os—H), -9.96 (br, 2H, Os—H). T$_{1(min)}$ (ms, OsH, 400 MHz, CD$_2$Cl$_2$): 115.0±11 (233 K). $^{13}$C {$^1$H}-APT NMR, HMBC and HSQC (100.6 MHz, C$_6$D$_6$, 293 K): δ 204.9 (t, J$_{C—P}$=5.6, NCN Bzm), 157.7 (t, J$_{C—P}$=6.7, Os—C Ph), 149.2 (s, N—C Ph), 148.0 (s, C—H Ph), 136.2 (s, C Bzm), 132.3 (s, C Bzm), 130.3 (s, C Bzm), 129.6 (s, C Bzm), 124.2 (s, C—H Ph), 119.8 (s, C—H Ph), 112.3 (s, C—H Ph), 111.6 (s, C—H Bzm), 110.2 (s, C—H Bzm), 36.8 (s, NCH$_3$), 28.1 (dvt, N=24.8, P—CH), 20.2 and 20.1 (both s, —CH$_3$ Bzm), 20.0 (s, PCH(CH$_3$)$_2$), 19.8 (s, PCH(CH$_3$)$_2$). $^{31}$P{$^1$H} NMR (162.0 MHz, C$_6$D$_6$, 293 K): δ 25.6 (s).

Table 2 below shows HOMO and LUMO levels for the Osmium complexes calculated by DFT (density function theory) calculation using Gaussian/B31yp/cep-31g.

TABLE 2

| Compound Number | Structure | HOMO(eV) | LUMO(eV) | T1(nm) |
|---|---|---|---|---|
| Comparative Compound 1 | 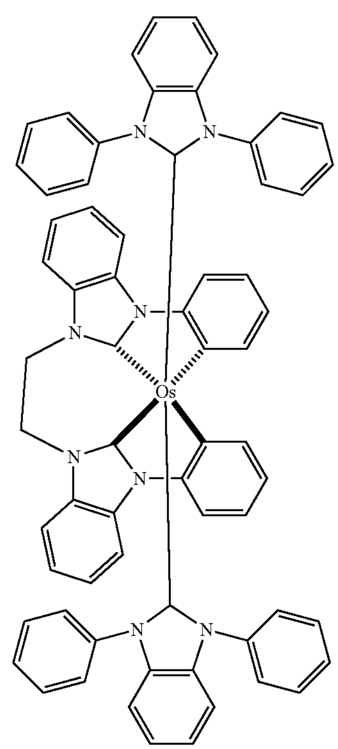 | −4.30 | −0.95 | 497 |

TABLE 2-continued

| Compound Number | Structure | HOMO(eV) | LUMO(eV) | T1(nm) |
|---|---|---|---|---|
| Comparative Compound 2 | 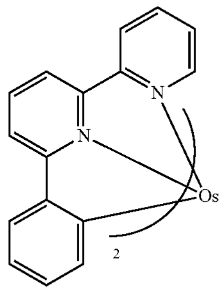 | −4.52 | −1.96 | 929 |
| Compound IV-3 | 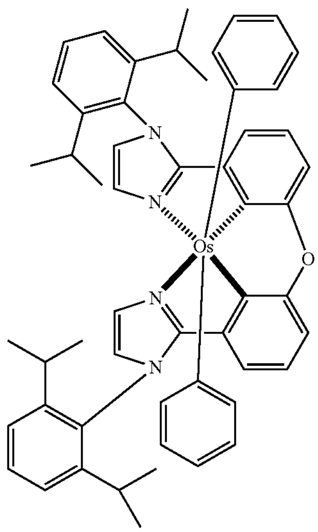 | −4.98 | −2.50 | 1296 |
| Compound I-1 | 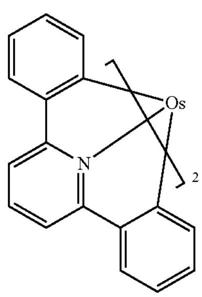 | −5.12 | −2.82 | 974 |
| Compound IV-5 | 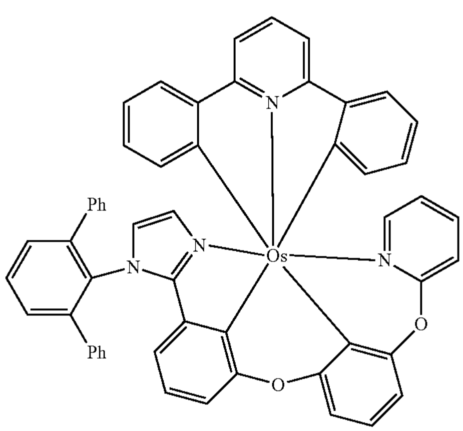 | −5.01 | −1.59 | 575 |

TABLE 2-continued
| Compound Number | Structure | HOMO(eV) | LUMO(eV) | T1(nm) |
| --- | --- | --- | --- | --- |
| Compound IV-4 | 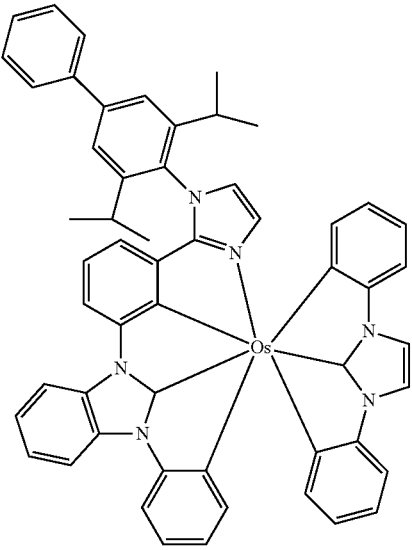 | −4.91 | −1.29 | 493 |
| Compound III-2 | 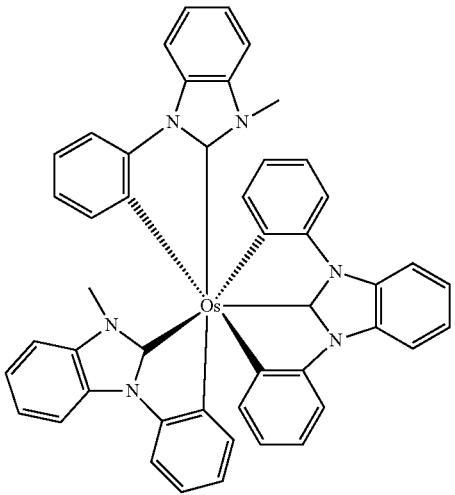 | −5.06 | −1.17 | 425 |
| Compound III-1 | 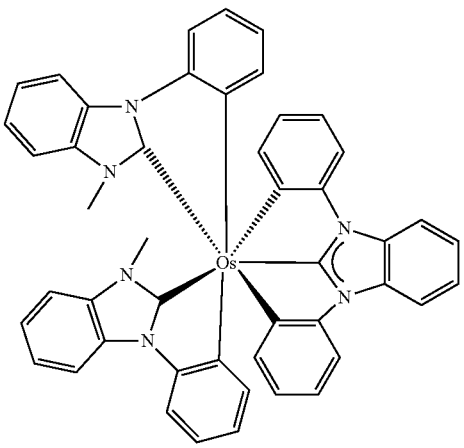 | −5.02 | −1.37 | 458 |

TABLE 2-continued

| Compound Number | Structure | HOMO(eV) | LUMO(eV) | T1(nm) |
|---|---|---|---|---|
| Compound IV-1 | 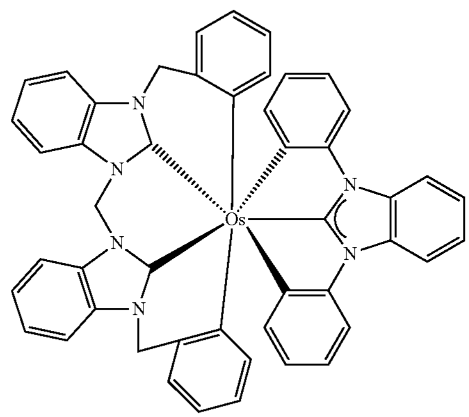 | −5.02 | −1.15 | 418 |
| Compound III-4 | 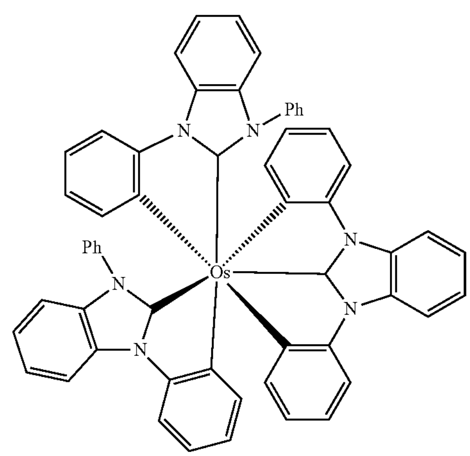 | −5.01 | −1.25 | 433 |
| Compound III-5 | 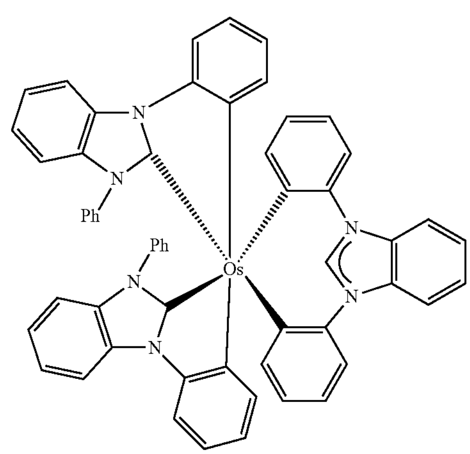 | −5.00 | −1.38 | 466 |

Osmium (II) complexes have been investigated for OLED applications. (see review: Eur. J. Inorg. Chem. 2006, 3319-3332). The octahedral ligand arrangement of the Os(II) complexes resembles that of Ir(III) complexes. Os(II) complexes generally exhibit low oxidation potential, i.e. shallow HOMO energy level than complexes. The extremely shallow HOMO level of Osmium bis(tridenate) complexes make it difficult to fit in the main stream OLED device structure. According to the invention disclosed in the present disclosure, by taking advantage of the higher oxidation state of Os(IV) relative to Os(II); the inventors found that Osmium (IV) complexes having more reasonable HOMO levels. i.e. a HOMO level around −5.0 eV. For example, comparative compounds 1 and 2 in Table 2, which are the osmium (II) complexes; the HOMO level is −4.3 eV and −4.52 eV individually. On the other hand; the rest of compounds in Table 2, which are the osmium (IV) complexes, the HOMO level is around −5.0 eV. Moreover, depending on the ligand environment, osmium (IV) can adopt face-capped octahedral, pentagonal bipyramidal, square-face capped trigonal prism, or trigonal-face capped trigonal prism configuration which can result in better flexibility for choice of ligands, making them suitable for display applications.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A compound having the formula Os(L)$_n$, wherein Os is osmium(IV) metal, L is a ligand coordinating to Os, and n is 2;

wherein each L can be same or different;

wherein L is a tridentate ligand selected from the group consisting of:

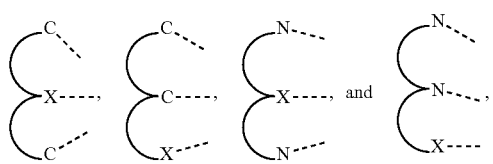

provided that at least one L is

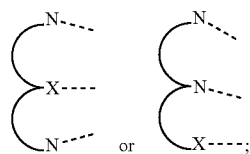

wherein X is a neutral coordinating atom selected from the group consisting of carbene, phosphorus, and nitrogen;
wherein C is an anionic coordinating carbon atom;
wherein N is an anionic coordinating nitrogen atom; and
wherein the compound is neutral.

2. The compound of claim 1, wherein the neutral carbene is N-heterocyclic carbene; wherein the neutral phosphorus is phosphorus atom of a trisubstituted phosphine; and wherein the neutral nitrogen is sp$^2$ nitrogen atom of N-heterocyclic ring selected from the group consisting of pyridine, imidazole, benzoimidazole, pyrazole, and triazole.

3. The compound of claim 1, wherein the anionic coordinating carbon is sp$^2$ carbon atom selected from the group consisting of benzene, pyridine, furan, thiophene, and pyrrole.

4. The compound of claim 1, wherein the anionic coordinating nitrogen is sp$^2$ nitrogen atom of N-heterocyclic ring selected from the group consisting of imidazole, benzoimidazole, pyrazole, and triazole.

5. The compound of claim 1, wherein the compound has a formula selected from the group consisting of:

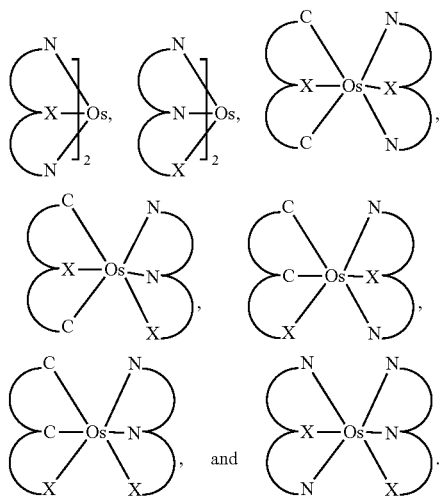

6. The compound of claim 5, wherein the compound is selected from the group consisting of Compound I-9

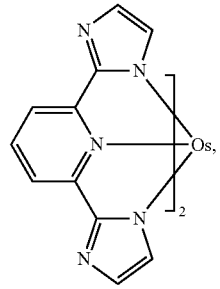

Compound I-10

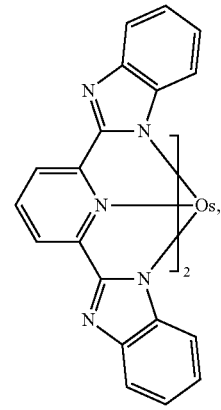

Compound I-11

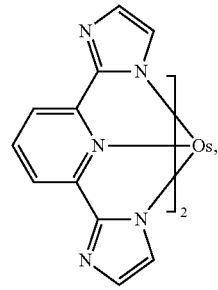

-continued

Compound I-21

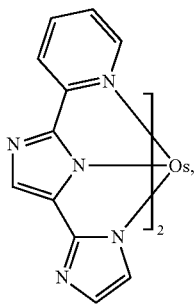

Compound I-22

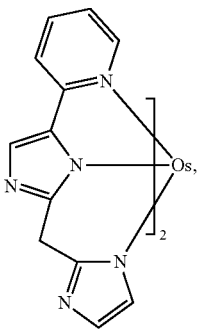

Compound I-25

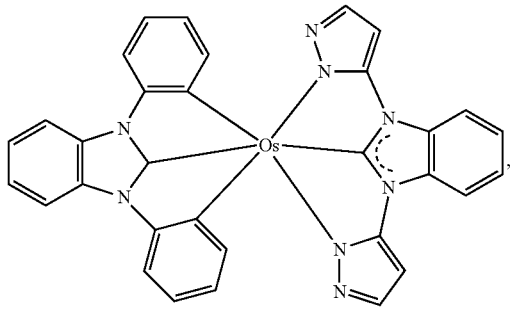

Compound I-26

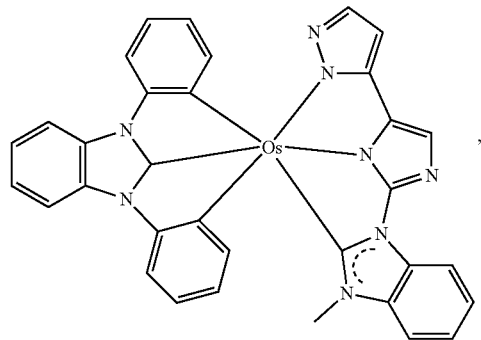

-continued

Compound I-27

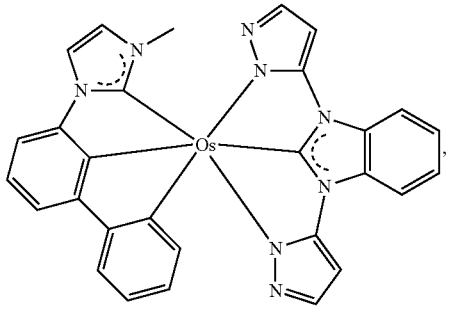

Compound I-28

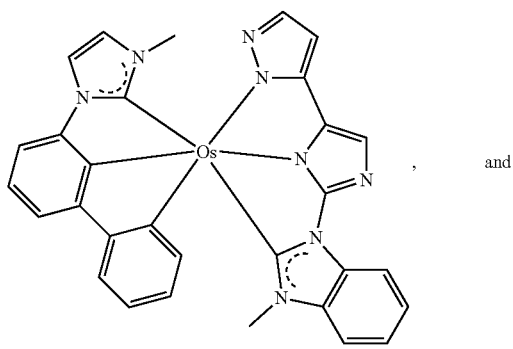

, and

Compound I-29

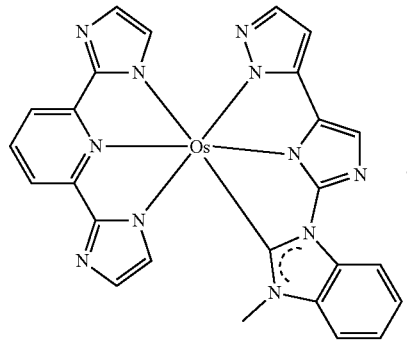

.

7. A first device comprising a first organic light emitting device, the first organic light emitting device comprising:
   an anode;
   a cathode; and
   an organic layer, disposed between the anode and the cathode, comprising a compound having the formula Os(L)n, wherein Os is Os(IV) metal, L is a ligand coordinating to Os, and n is 2;
   wherein each L can be same or different;
   wherein L is a tridentate ligand selected from the group consisting of:

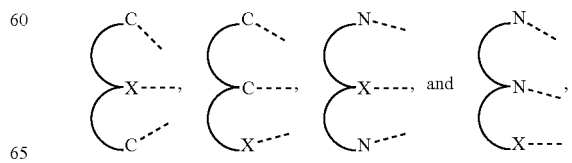

provided that at least one L is

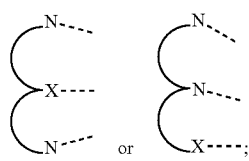

wherein X is a neutral coordinating atom selected from the group consisting of carbene, phosphorus, and nitrogen;

wherein C is an anionic coordinating carbon atom;

wherein N is an anionic coordinating nitrogen atom; and wherein the compound is neutral.

8. The first device of claim 7, wherein the first device is a consumer product.

9. The consumer product according to claim 8, wherein the consumer product is selected from the group consisting of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, a personal digital assistant (PDA), a laptop computer, a digital camera, a camcorder, a viewfinder, a micro-display, a 3-D display, a vehicle, a theater or stadium screen, and a sign.

10. The first device of claim 7, wherein the first device is an organic light emitting device.

11. The first device of claim 7, wherein the first device comprises a light panel.

12. The first device of claim 7, wherein the organic layer is an emissive layer and the compound is an emissive dopant.

13. The first device of claim 7, wherein the organic layer is an emissive layer and the compound is a non-emissive dopant.

14. The first device of claim 7, wherein the organic layer further comprises a host material.

15. The first device of claim 14, wherein the host material comprises a triphenylene containing benzo-fused thiophene or benzo-fused furan;

wherein any substituent in the host material is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, and $C_nH_{2n}-Ar_1$, or the host has no substitutions;

wherein n is from 1 to 10; and wherein $Ar_1$ and $Ar_2$ are independently selected from the group consisting of benzene, biphenyl, naphthalene, triphenylene, carbazole, and heteroaromatic analogs thereof.

16. The first device of claim 14, wherein the host material comprises at least one chemical group selected from the group consisting of carbazole, dibenzothiphene, dibenzofuran, dibenzoselenophene, azacarbazole, aza-dibenzothiophene, aza-dibenzofuran, and aza-dibenzoselenophene.

17. The first device of claim 14, wherein the host material is selected from the group consisting of:

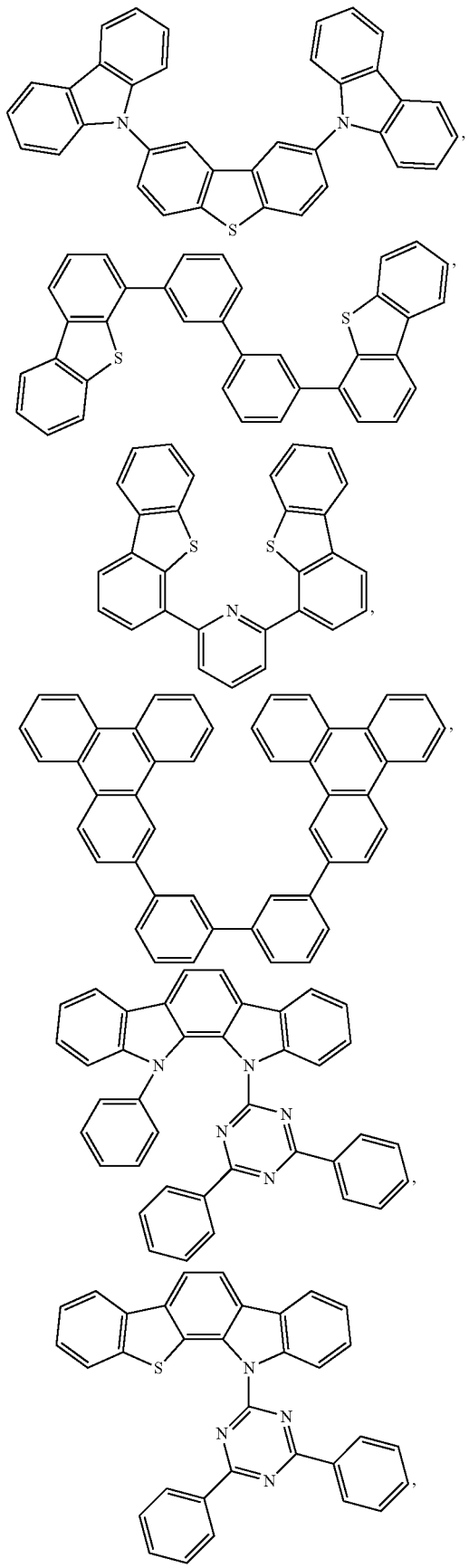

-continued

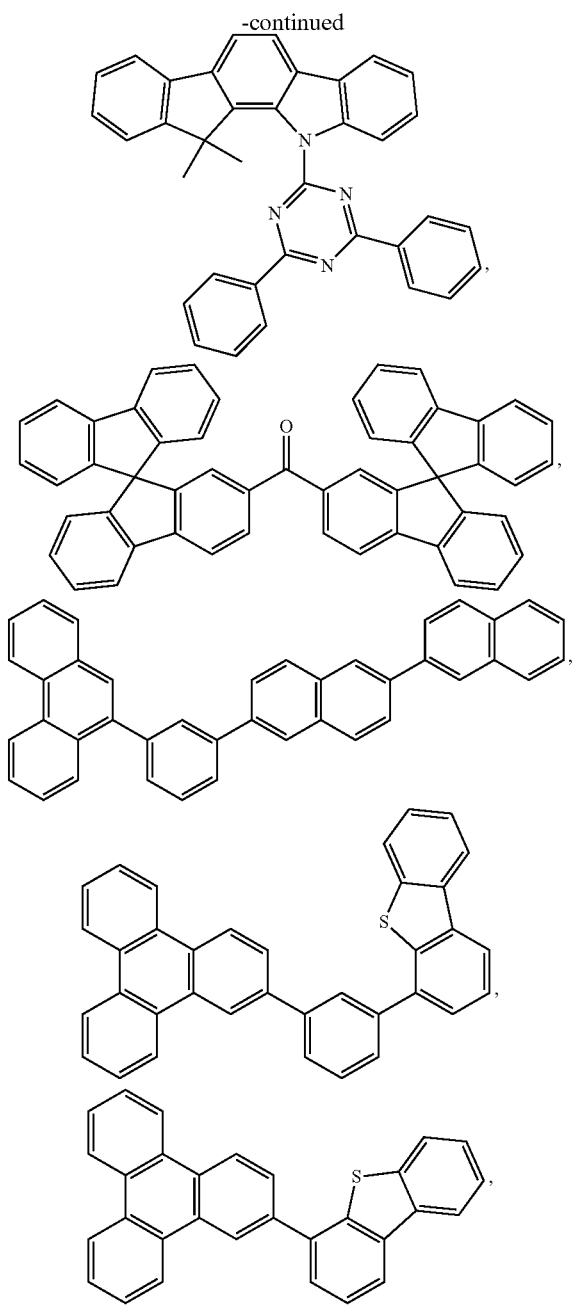

and combinations thereof.

18. The first device of claim 14, wherein the host material comprises a metal complex.

19. A consumer product comprising an organic light-emitting device comprising:

an anode;

a cathode; and an organic layer, disposed between the anode and the cathode, comprising a compound having the formula $Os(L)_n$, wherein Os is osmium(IV) metal, L is a ligand coordinating to Os, and n is 2;

wherein each L can be same or different;

wherein L is a tridentate ligand selected from the group consisting of:

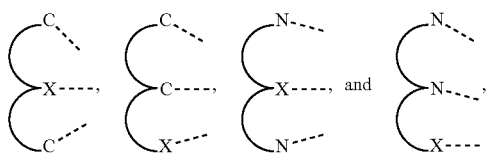

provided that at least one L is

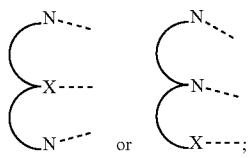

wherein X is a neutral coordinating atom selected from the group consisting of carbene, phosphorus, and nitrogen;

wherein C is an anionic coordinating carbon atom;

wherein N is an anionic coordinating nitrogen atom; and wherein the compound is neutral.

* * * * *

UNITED STATES PATENT AND TRADEMARK OFFICE
CERTIFICATE OF CORRECTION

PATENT NO. : 10,069,090 B2
APPLICATION NO. : 14/075653
DATED : September 4, 2018
INVENTOR(S) : Tsai et al.

Page 1 of 1

It is certified that error appears in the above-identified patent and that said Letters Patent is hereby corrected as shown below:

In the Claims

In Claim 6, Column 120, Lines 55-68, please delete the compound

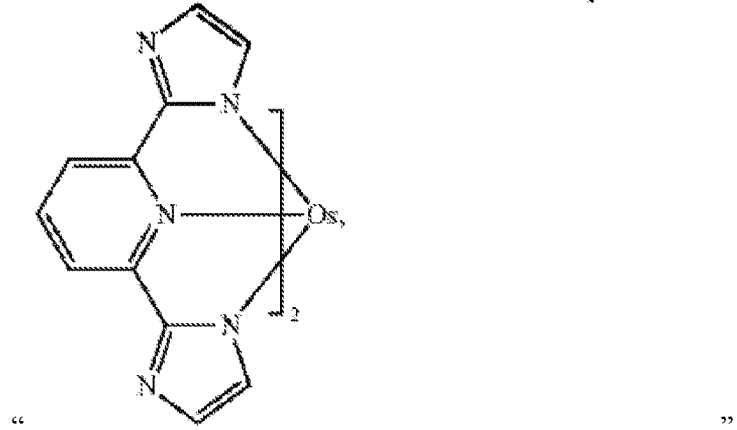

"  "

and insert -- 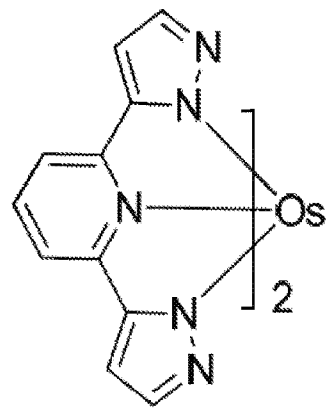 Compound I-11, --

Signed and Sealed this
Fourth Day of December, 2018

Andrei Iancu
*Director of the United States Patent and Trademark Office*